United States Patent
Day et al.

(10) Patent No.: US 12,420,009 B2
(45) Date of Patent: *Sep. 23, 2025

(54) PATIENT CARE SYSTEM WITH CONDITIONAL ALARM FORWARDING

(71) Applicant: ICU Medical, Inc., San Clemente, CA (US)

(72) Inventors: William Kenneth Day, Hoffman Estates, IL (US); Steve Joseph Lindo, Chicago, IL (US); Paul John Foryt, Woodstock, IL (US); Justin Joseph Schmidt, Grayslake, IL (US); Robert Cousineau, Boston, MA (US); Michael Kremliovsky, Poway, CA (US); Sumant Ramachandra, Northbrook, IL (US); Anatoly S. Belkin, Glenview, IL (US); Gary Mills, Escondido, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/756,704

(22) Filed: Jun. 27, 2024

(65) Prior Publication Data

US 2024/0424197 A1 Dec. 26, 2024

Related U.S. Application Data

(63) Continuation of application No. 18/121,855, filed on Mar. 15, 2023, now Pat. No. 12,042,623, which is a (Continued)

(51) Int. Cl.
*A61M 5/142* (2006.01)
*G08B 21/04* (2006.01)
(Continued)

(52) U.S. Cl.
CPC ......... *A61M 5/142* (2013.01); *G08B 21/0461* (2013.01); *G16H 20/17* (2018.01);
(Continued)

(58) Field of Classification Search
None
See application file for complete search history.

(56) References Cited

U.S. PATENT DOCUMENTS

| 4,024,864 A | 5/1977 | Davies et al. |
| 4,055,175 A | 10/1977 | Clemens et al. |

(Continued)

FOREIGN PATENT DOCUMENTS

| AU | 2004226440 | 10/2004 |
| AU | 2004305087 | 7/2005 |

(Continued)

OTHER PUBLICATIONS

Sethia et al., "Security Framework for Portable NFC Mobile Based Health Record System", Oct. 2016, IEEE 12th International Conference on Wireless and Mobile Computing, Networking and Communications, pp. 1-8.

(Continued)

*Primary Examiner* — John F Mortell
(74) *Attorney, Agent, or Firm* — Knobbe, Martens, Olson & Bear, LLP

(57) ABSTRACT

A patient care system is disclosed that includes a medical device such as an infusion pump. The medical device generates a data message containing information such as the status of the therapy being delivered, operating data or both. An alarm generating system assesses the data message from the pump and generates an alarm message if certain conditions established by a first set of rules are met. The alarm message is assessed according to a second set of rules as to whether to suppress the alarm message. The data message (Continued)

contains a required input for both the first and second algorithms. A dispatching system is adapted to forward the alarm message to an alarm destination according to a third set of rules. The alarm destination expresses an alarm upon receipt of the alarm message.

18 Claims, 10 Drawing Sheets

Related U.S. Application Data continuation of application No. 17/157,597, filed on Jan. 25, 2021, now Pat. No. 11,628,246, which is a continuation of application No. 16/846,882, filed on Apr. 13, 2020, now Pat. No. 10,898,641, which is a continuation of application No. 16/408,272, filed on May 9, 2019, now Pat. No. 10,617,815, which is a continuation of application No. 15/674,889, filed on Aug. 11, 2017, now Pat. No. 10,300,194, which is a continuation of application No. 14/700,357, filed on Apr. 30, 2015, now Pat. No. 9,764,082.

(60) Provisional application No. 61/986,562, filed on Apr. 30, 2014.

(51) Int. Cl.
*G16H 20/17* (2018.01)
*G16H 40/63* (2018.01)
*G16H 40/67* (2018.01)
*G16H 50/70* (2018.01)

(52) U.S. Cl.
CPC ............ *G16H 40/63* (2018.01); *G16H 40/67* (2018.01); *G16H 50/70* (2018.01); *A61M 2205/18* (2013.01); *A61M 2205/3553* (2013.01); *A61M 2205/3584* (2013.01); *A61M 2205/3592* (2013.01); *A61M 2205/52* (2013.01)

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |

(56) References Cited

U.S. PATENT DOCUMENTS

| | | |
|---|---|---|
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,708,714 A | 1/1998 | Lopez et al. |
| 5,713,350 A | 2/1998 | Yokota et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,365 A | 9/2000 | Newberg |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |

(56) References Cited

U.S. PATENT DOCUMENTS

| | | |
|---|---|---|
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |

(56) References Cited

U.S. PATENT DOCUMENTS

| | | | |
|---|---|---|---|
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,126,730 B2 | 2/2012 | Dicks et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,486,019 B2 | 7/2013 | White et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |

(56) References Cited

U.S. PATENT DOCUMENTS

| | | |
|---|---|---|
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Blomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |
| 9,430,655 B1 | 8/2016 | Stockton et al. |
| 9,438,580 B2 | 9/2016 | Kupper |
| 9,483,615 B2 | 11/2016 | Roberts |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,717,845 B2 | 8/2017 | Istoc |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,967,739 B2 | 5/2018 | Proennecke et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,173,008 B2 | 1/2019 | Simpson et al. |
| 10,188,849 B2 | 1/2019 | Fangrow |
| 10,233,179 B2 | 3/2019 | Ng et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,341,866 B1 | 7/2019 | Spencer et al. |
| 10,409,995 B1 | 9/2019 | Wasiq |
| 10,430,761 B2 | 10/2019 | Hume et al. |
| 10,434,246 B2 | 10/2019 | Silkaitis et al. |
| 10,438,001 B1 | 10/2019 | Hariprasad |
| 10,452,842 B2 | 10/2019 | Dhondse |
| 10,453,157 B2 | 10/2019 | Kamen et al. |
| 10,463,788 B2 | 11/2019 | Day |
| 10,516,536 B2 | 12/2019 | Rommel |
| 10,617,815 B2 | 4/2020 | Day et al. |
| 10,646,651 B2 | 5/2020 | Day et al. |
| 10,681,207 B1 | 6/2020 | Johnson et al. |
| 10,692,595 B2 | 6/2020 | Xavier et al. |
| 10,728,262 B1 | 7/2020 | Vaswani |
| 10,740,436 B2 | 8/2020 | Moskal et al. |
| 10,741,280 B2 | 8/2020 | Xavier et al. |
| 10,757,219 B2 | 8/2020 | Moskal |
| 10,765,799 B2 | 9/2020 | Belkin et al. |
| 10,799,632 B2 | 10/2020 | Kohlbrecher |
| 10,812,380 B2 | 10/2020 | Jha et al. |
| 10,861,592 B2 | 12/2020 | Xavier et al. |
| 10,898,641 B2 | 1/2021 | Day et al. |
| 10,950,339 B2 | 3/2021 | Xavier et al. |
| 10,964,428 B2 | 3/2021 | Xavier et al. |
| 11,013,861 B2 | 5/2021 | Wehba et al. |
| 11,037,668 B2 | 6/2021 | Ruchti et al. |
| 11,052,193 B2 | 7/2021 | Day et al. |
| 11,139,058 B2 | 10/2021 | Xavier et al. |
| 11,151,290 B2 | 10/2021 | Karakoyunlu et al. |
| 11,152,108 B2 | 10/2021 | Xavier et al. |
| 11,152,109 B2 | 10/2021 | Xavier et al. |
| 11,152,110 B2 | 10/2021 | Xavier et al. |
| 11,194,810 B2 | 12/2021 | Butler et al. |
| 11,235,100 B2 | 2/2022 | Howard et al. |
| 11,289,183 B2 | 3/2022 | Kohlbrecher |
| 11,309,070 B2 | 4/2022 | Xavier et al. |
| 11,328,804 B2 | 5/2022 | Xavier et al. |
| 11,328,805 B2 | 5/2022 | Xavier et al. |
| 11,373,753 B2 | 6/2022 | Xavier et al. |
| 11,437,132 B2 | 9/2022 | Xavier et al. |
| 11,470,000 B2 | 10/2022 | Jha et al. |
| 11,483,402 B2 | 10/2022 | Xavier et al. |
| 11,483,403 B2 | 10/2022 | Xavier et al. |
| 11,501,877 B2 | 11/2022 | Kohlbrecher et al. |
| 11,571,508 B2 | 2/2023 | Jacobson et al. |
| 11,574,721 B2 | 2/2023 | Kohlbrecher |
| 11,574,737 B2 | 2/2023 | Dharwad et al. |
| 11,587,669 B2 | 2/2023 | Xavier et al. |
| 11,590,057 B2 | 2/2023 | Tagliamento et al. |
| 11,594,326 B2 | 2/2023 | Xavier et al. |
| 11,605,468 B2 | 3/2023 | Jacobson et al. |
| 11,626,205 B2 | 4/2023 | Arrizza et al. |
| 11,628,246 B2 | 4/2023 | Day et al. |
| 11,628,254 B2 | 4/2023 | Day et al. |
| 11,654,237 B2 | 5/2023 | Wehba et al. |
| 11,670,416 B2 | 6/2023 | Xavier et al. |
| 11,763,927 B2 | 9/2023 | Ruchti et al. |
| 11,783,935 B2 | 10/2023 | Xavier et al. |
| 11,881,297 B2 | 1/2024 | Xavier et al. |
| 11,923,076 B2 | 3/2024 | Xavier et al. |
| 11,986,623 B2 | 5/2024 | Jacobson et al. |
| 11,996,188 B2 | 5/2024 | Arrizza et al. |
| 12,002,562 B2 | 6/2024 | Kohlbrecher |
| 12,036,390 B2 | 7/2024 | Wehba et al. |
| 12,040,068 B2 | 7/2024 | Xavier et al. |
| 12,042,623 B2 | 7/2024 | Day et al. |
| 12,042,631 B2 | 7/2024 | Day et al. |
| 12,046,361 B2 | 7/2024 | Xavier et al. |
| 12,047,292 B2 | 7/2024 | Jha et al. |
| 12,097,351 B2 | 9/2024 | Belkin et al. |
| 12,130,910 B2 | 10/2024 | Vivek et al. |
| 12,142,370 B2 | 11/2024 | Xavier et al. |
| 12,205,702 B2 | 1/2025 | Xavier et al. |
| 2001/0016056 A1 | 8/2001 | Westphal et al. |
| 2001/0029178 A1 | 10/2001 | Criss et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |

(56) References Cited

U.S. PATENT DOCUMENTS

| | | |
|---|---|---|
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0021700 A1 | 2/2002 | Hata et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0044043 A1 | 4/2002 | Chaco et al. |
| 2002/0044059 A1 | 4/2002 | Reeder et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0154600 A1 | 10/2002 | Ido et al. |
| 2002/0173702 A1 | 11/2002 | Lebel et al. |
| 2002/0173875 A1 | 11/2002 | Wallace et al. |
| 2002/0193679 A1 | 12/2002 | Malave et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0036744 A1 | 2/2003 | Struys et al. |
| 2003/0047126 A1 | 3/2003 | Tomaschko |
| 2003/0047600 A1 | 3/2003 | Nakanishi et al. |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019464 A1 | 1/2004 | Martucci et al. |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |

(56) References Cited

U.S. PATENT DOCUMENTS

| | | |
|---|---|---|
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0253554 A1 | 11/2006 | Uwais |
| 2006/0258985 A1 | 11/2006 | Russell |
| 2006/0259327 A1 | 11/2006 | Hoag |
| 2006/0264895 A1 | 11/2006 | Flanders |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0073822 A1 | 3/2007 | Bennett et al. |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0229249 A1* | 10/2007 | McNeal ............... A61B 5/0002 340/524 |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0240215 A1 | 10/2007 | Flores |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |

(56) References Cited

U.S. PATENT DOCUMENTS

| | | |
|---|---|---|
| 2008/0275384 A1 | 11/2008 | Mastrototaro et al. |
| 2008/0300572 A1* | 12/2008 | Rankers ............ A61B 5/14532 604/504 |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099866 A1 | 4/2009 | Newman |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0106318 A1 | 5/2011 | Ledford et al. |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289162 A1 | 11/2011 | Furlong |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1 | 2/2012 | Rodriguez |
| 2012/0066501 A1 | 3/2012 | Xiong |
| 2012/0070045 A1 | 3/2012 | Vesper et al. |
| 2012/0079084 A1 | 3/2012 | Forssell et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |

(56) References Cited

U.S. PATENT DOCUMENTS

| | | |
|---|---|---|
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0116578 A1 | 5/2013 | An |
| 2013/0133083 A1 | 5/2013 | Kurumai |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 * | 10/2013 | Gross .................. H04L 51/214 709/206 |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0108783 A1 | 4/2014 | Suzuki |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0194817 A1 | 7/2014 | Lee et al. |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0288947 A1 | 9/2014 | Simpson et al. |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0366878 A1 | 12/2014 | Baron |
| 2014/0371543 A1 | 12/2014 | Steinhauer et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0207626 A1 | 7/2015 | Neftel et al. |
| 2015/0220890 A1 | 8/2015 | Seshadri et al. |
| 2015/0230760 A1 | 8/2015 | Schneider |
| 2015/0281128 A1 | 10/2015 | Sindhu |
| 2015/0325064 A1 | 11/2015 | Downey |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0063471 A1 | 3/2016 | Kobres et al. |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2016/0378618 A1 | 12/2016 | Cmielowski |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0140134 A1 | 5/2017 | Brough et al. |
| 2017/0146381 A1 | 5/2017 | Eckel et al. |
| 2017/0147761 A1 | 5/2017 | Moskal et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0325091 A1 | 11/2017 | Freeman et al. |
| 2017/0331804 A1 | 11/2017 | Jellison et al. |
| 2017/0351841 A1 | 12/2017 | Moskal |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0157821 A1 | 6/2018 | Fan |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0166501 A1 | 5/2019 | Debates et al. |
| 2019/0172590 A1 | 6/2019 | Vesto et al. |
| 2019/0207965 A1 | 7/2019 | Espinosa |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0269852 A1 | 9/2019 | Kohlbrecher |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027542 A1 | 1/2020 | Xavier et al. |
| 2020/0027543 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0028914 A1 | 1/2020 | Xavier et al. |
| 2020/0028929 A1 | 1/2020 | Xavier et al. |
| 2020/0035355 A1 | 1/2020 | Xavier et al. |
| 2020/0054825 A1 | 2/2020 | Kamen et al. |
| 2020/0061291 A1 | 2/2020 | Day et al. |
| 2020/0118692 A1 | 4/2020 | Booker et al. |

(56) References Cited

U.S. PATENT DOCUMENTS

| | | | |
|---|---|---|---|
| 2020/0145332 A1 | 5/2020 | Jha et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0330685 A1 | 10/2020 | Day |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0043296 A1 | 2/2021 | Xavier et al. |
| 2021/0045640 A1 | 2/2021 | Poltorak |
| 2021/0050097 A1 | 2/2021 | Xavier et al. |
| 2021/0085855 A1 | 3/2021 | Belkin et al. |
| 2021/0098106 A1 | 4/2021 | Kohlbrecher et al. |
| 2021/0098107 A1 | 4/2021 | Xavier et al. |
| 2021/0105206 A1 | 4/2021 | Jha et al. |
| 2021/0316072 A1 | 10/2021 | Wehba et al. |
| 2021/0358603 A1 | 11/2021 | Xavier et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0023535 A1 | 1/2022 | Day |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0139538 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2022/0384059 A1 | 12/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0166026 A1 | 6/2023 | Jacobson et al. |
| 2023/0188465 A1 | 6/2023 | Jha et al. |
| 2023/0253108 A1 | 8/2023 | Dharwad et al. |
| 2023/0298768 A1 | 9/2023 | Jacobson et al. |
| 2023/0320935 A1 | 10/2023 | Tagliamento |
| 2023/0321350 A1 | 10/2023 | Day et al. |
| 2023/0321351 A1 | 10/2023 | Wehba et al. |
| 2023/0326570 A1 | 10/2023 | Kohlbrecher |
| 2023/0410989 A1 | 12/2023 | Xavier et al. |
| 2024/0038358 A1 | 2/2024 | Xavier et al. |
| 2024/0047035 A1 | 2/2024 | Ruchti et al. |
| 2024/0071609 A1 | 2/2024 | Rohlwing |
| 2024/0293610 A1 | 9/2024 | Jacobson |
| 2024/0347161 A1 | 10/2024 | Kohlbrecher |
| 2024/0363236 A1 | 10/2024 | Arrizza et al. |
| 2024/0390583 A1 | 11/2024 | Wehba et al. |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 050 993 | 11/2000 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | I631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |

(56) References Cited

FOREIGN PATENT DOCUMENTS

| | | |
|---|---|---|
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |

OTHER PUBLICATIONS

International Search Report and Written Opinion received in PCT Application No. PCT/US2015/028551, dated Jul. 29, 2015 in 10 pages.

International Preliminary Report on Patentability and Written Opinion received in PCT Application No. PCT/US2015/028551, dated Nov. 10, 2016 in 9 pages.

Ahn et al., "Towards Scalable Authentication in Health Services", Eleventh IEEE International Workshops on Enabling Technologies: Infrastructure for Collaborative Enterprises, Jun. 2002, pp. 83-88.

Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., Corn, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bellare et al., "Security Proofs for Identity-Based Identification and Signature Schemes", Lecture Notes in Computer Science, Jan. 2009, vol. 22, No. 1, pp. 18.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.

"CareAware® Infusion Management", Cerner Store, as printed May 12, 2011, pp. 3, <https://store.cerner.com/items/7>.

(56) References Cited

OTHER PUBLICATIONS

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

"Context-Free Grammar", Wikipedia.org, as last modified Mar. 5, 2010 in 11 pages, <https://en.wikipedia.org/w/index.php/?title=Context-free_grammar&oldid=347915989>.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

Doesburg et al., "Improved Usability of a Multi-Infusion Setup Using a Centralized Control Interface: A Task-Based Usability Test", Aug. 11, 2017, PLoS One, vol. 12, No. 8, pp. 10.

"Download", Free On-Line Dictionary of Computing, as archived Jun. 16, 2010 in 1 page, http://web.archive.org/web/20100616010314/https://foldoc.org/download.

East PhD et al., "Digital Electronic Communication Between ICU Ventilators and Computers and Printers", Respiratory Care, Sep. 1992, vol. 37, No. 9, pp. 1113-1122.

Edworthy, Judy, "Medical Audible Alarms: A Review", Journal of the American Medical Informatics Association, vol. 20, No. 3, 2013, pp. 584-589.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification", Wikipedia.org, as last modified Oct. 11, 2011 in 2 pages, <https://en.wikipedia.org/w/index.php?title=File_verification&oldid=455048290>.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D. et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.

Glaeser, "A Hierarchical Minicomputer System for Continuous Post-Surgical Monitoring", Computers and Biomedical Research, Aug. 31, 1975, pp. 336-361.

Goldberg et al., "Clinical Results of an Updated Insulin Infusion Protocol in Critically Ill Patients", Diabetes Spectrum, 2005, vol. 18, No. 3, pp. 188-191.

Gomez et al., "CLAM: Connection-Less, Lightweight, and Multiway Communication Support for Distributed Computing", Computer Science, 1997, vol. 1199, pp. 227-240.

"GPS Tracker for Medical Equipment", <http://www.trackingsystem.com/forbusinesses/corporate-trackingsystem/1098-gps-tracker-formedicalequipment.html>, Mar. 15, 2015, pp. 2.

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.

Gutwin et al., "Gone But Not Forgotten: Designing for Disconnection in Synchronous Groupware", CSCW 2010, Feb. 6-10, 2010, Savannah, Georgia, USA., pp. 179-188.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hamann et al., "Pumpsim: A Software Package for Simulating Computer-Controlled Drug Infusion Pumps", Annual International Conference of the IEEE Engineering in Medicine and Biology Society, 1990, vol. 12, No. 5, pp. 2019-2020.

Hasegawa et al., "On a Portable Memory Device for Physical Activities and Informations of Maternal Perception", Journal of Perinatal Medicine, 1988, vol. 16, No. 4, pp. 349-356.

Hawley et al., "Clinical Implementation of an Automated Medical Information Bus in an Intensive Care Unit", Proceedings of the Annual Symposium on Computer Application in Medical Care, Nov. 9, 1988, pp. 621-624.

Hayes-Roth et al., "Guardian: A Prototype Intelligent Agent for Intensive-Care Monitoring", Artificial Intelligence in Medicine, vol. 4, Dec. 31, 1992, pp. 165-185.

Hospira, GemStar® Pain Management Infusion System 9-084-PR1-2-2, <www.hospira.com/products/gemstar_painmanagement.aspx>, Jan. 28, 2010, pp. 1-2.

Huang et al., "Secure Identity-Based Data Sharing and Profile Matching for Mobile Healthcare Social Networks in Cloud Computing", vol. 6, Jul. 2018, pp. 36584-36594.

Introducing Abbott TQPM (Total Quality Pain Management), Abbott Laboratories, Abbott Park, IL, May 2000, pp. 1-4.

"Infusion Pump", Wikipedia.org, as last modified Mar. 27, 2014, in 3 pages, <https://web.archive.org/web/20140703024932/https://en.wikipedia.org/wiki/Infusion_pump>.

Isaka et al., "Control Strategies for Arterial Blood Pressure Regulation", IEEE Transactions on Biomedical Engineering, Apr. 1993, vol. 40, No. 4, pp. 353-363.

Johnson et al., "Using BCMA Software to Improve Patient Safety in Veterans Administration Medical Centers", Journal of Healthcare Information Management, Dec. 6, 2004, vol. 16, No. 1, pp. 46-51.

Kent Displays, "Reflex ™ Electronic Skins", Product Brief 25127B, 2009, pp. 2.

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

(56) References Cited

OTHER PUBLICATIONS

Li et al., "Hijacking an Insulin Pump: Security Attacks and Defenses for a Diabetes Therapy System", 2011 IEEE 13th International Conference on e-Health Networking, Applications and Services, 2011, pp. 150-156.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and Alaris Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Michienzi, Kelly, "Managing Drug Library Updates", Pharmacy Purchasing Products, https://www.pppmag.com/article/1061, Feb. 2012, vol. 9, pp. 22-23.
Micrel Medical Devices, "MP Daily +" <http://web.archive.org/web/20130803235715/http://www.micrelmed.com/index.aspx?productid=9> as archived Aug. 3, 2013 in 1 page.
Moghissi, Etie, MD, FACP, Face, "Hyperglycemia in Hospitalized Patients", A Supplement to ACP Hospitalist, Jun. 15, 2008, pp. 32.
Murphy, Robert, "The Design of Safety-Critical Medical Infusion Devices", May 30, 2007, Doctor of Philosophy submission, pp. 317.
Murray, Jr. et al., "Automated Drug Identification System (during surgery)", IEEE Proceedings of Southeastcon '91, Apr. 7-10, 1991, pp. 265.
Nicholson et al., "Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nojoumian et al., "Social Secret Sharing in Cloud Computing Using a New Trust Function", 2012 Tenth Annual International Conference on Privacy, Security and Trust, pp. 161-167.
Nolan et al., "The P1073 Medical Information Bus Standard: Overview and Benefits for Clinical Users", 1990, pp. 216-219.
Omnilink Systems, Inc., "Portable Medical Equipment Tracking", <http://www.omnilink.com/portablemedicalequipmenttracking/>, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, <http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2>, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", May 15, 2008, pp. 63. <https://usme.com/content/manuals/sigma-spectrum-operator-manual.pdf>.
"Sigma Spectrum: Operator's Manual", Oct. 2009, pp. 72. <http://static.medonecapital.com/manuals/userManuals/Sigma-Spectrum-Operator-Manual-Oct. 2009.pdf>.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Set-

(56) References Cited

OTHER PUBLICATIONS ting", Hospital Pharmacy, Sep. 2007, vol. 42, No. 9, pp. 832-840. <http://www.thomasland.com/hpj4209-832.pdf>.

Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.

Smith, Joe, "Infusion Pump Informatics", CatalyzeCare: Transforming Healthcare, as printed May 12, 2011, pp. 2.

Sodders, Lisa, "VA Center Keeps Medicine in Right Hands", The Capital-Journal, Dec. 4, 1999, pp. 1-2.

"Software Versioning", Wikipedia.org, dated Oct. 16, 2011 in 11 pages, <https://en.wikipedia.org/w/index.php?title=Software_versioning&oldid=455859110>.

Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.

Stitt, F.W., "The Problem-Oriented Medical Synopsis: a Patient-Centered Clinical Information System", Proceedings of the Annual Symposium on Computer Application in Medical Care, 1994, pp. 88-92.

Stokowski, Laura A. RN, MS, "Using Technology to Improve Medication Safety in the Newborn Intensive Care Unit", Advances in Neonatal Care, Dec. 2001, vol. 1, No. 2, pp. 70-83.

Sutton et al., "The Syntax and Semantics of the PROforma Guideline Modeling Language", Journal of the American Medical Informatics Association, Sep./Oct. 2003, vol. 10, No. 5, pp. 433-443.

Szeinbach et al., "Automated Dispensing Technologies: Effect on Managed Care", Journal of Managed Care Pharmacy (JMCP), Sep./Oct. 1995, vol. 1, No. 2, pp. 121-127.

Szolovits et al., "Guardian Angel: Patient-Centered Health Information Systems", Technical Report MIT/LCS/TR-604, Massachusetts Institute of Technology Laboratory for Computer Science, May 1994, pp. 39.

"TCG TPM v2.0 Provisioning Guidance", Reference, Version 1, Revision 1, Mar. 15, 2017, pp. 1-43.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Van Der Maas et al., "Requirements for Medical Modeling Languages", Journal of the American Medical Informatics Association, Mar./Apr. 2001, vol. 8, No. 2, pp. 146-162.

Villalobos et al., "Computerized System in Intensive Care medicine", Medical Informatics, vol. 11, No. 3, 1986, pp. 269-275.

Wilkins et al., "A Regular Language: The Annotated Case Report Form", PPD Inc., PharmaSUG2011—Paper CD18, 2011, pp. 1-9.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.

Yoo et al., "Code-Based Authentication Scheme for Lightweight Integrity Checking of Smart Vehicles", IEEE Access, 2018, vol. 6, pp. 46731-46741.

Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.

Yurkonis et al., "Computer Simulation of Adaptive Drug Infusion", IEEE Transactions on Biomedical Engineering, vol. BME-34, No. 8, Aug. 1987, pp. 633-635.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

Fan et al., "Smart Medication Delivery Systems: Infusion Pumps", Supplementary Report, Healthcare Human Factors, Feb. 26, 2010, pp. 94.

\* cited by examiner

PATIENT CARE SYSTEM WITH CONDITIONAL ALARM FORWARDING

CROSS-REFERENCE TO RELATED APPLICATIONS

This application is a continuation of U.S. patent application Ser. No. 18/121,855, entitled "Patient Care System with Conditional Alarm Forwarding," filed Mar. 15, 2023, which is a continuation of U.S. patent application Ser. No. 17/157,597, entitled "Patient Care System with Conditional Alarm Forwarding," filed Jan. 25, 2021, which is a continuation of U.S. patent application Ser. No. 16/846,882, entitled "Patient Care System with Conditional Alarm Forwarding," filed Apr. 13, 2020, which is a continuation of U.S. patent application Ser. No. 16/408,272, entitled "Patient Care System with Conditional Alarm Forwarding," filed May 9, 2019, which is a continuation of U.S. patent application Ser. No. 15/674,889, entitled "Patient Care System with Conditional Alarm Forwarding," filed Aug. 11, 2017, which is a continuation of U.S. patent application Ser. No. 14/700,357, entitled "Patient Care System with Conditional Alarm Forwarding," filed Apr. 30, 2015, which claims the benefit of priority to U.S. Provisional Patent Application No. 61/986,562, entitled "Patient Care System with Conditional Alarm Forwarding," filed Apr. 30, 2014, the disclosures of which are hereby incorporated by reference in their entirety.

BACKGROUND

Modern medical care often involves the use of medication management systems that include medication delivery and monitoring devices such as medication delivery pumps or patient parameter monitors or both, Medication management systems for configuring, controlling and monitoring medication delivery devices have been disclosed. For example, commonly owned U.S. Pat. No. 7,895,053 titled "MEDICATION MANAGEMENT SYSTEM" that issued on Feb. 22, 2011 and U.S. patent application Ser. No. 10/783,573 titled "MEDICATION MANAGEMENT SYSTEM" that published as US20050278194A1 on Dec. 15, 2005 disclose a medication management system wherein user customizable drug library or medical device configuration information is prepared using a drug library editor (DLE) program and module of a medication management unit (MMU). Hospira MedNet™ Meds™ software available from Hospira, Inc. of Lake Forest, IL, U.S.A. includes such a DLE program. The MMU, which is equipped with Hospira MedNet™ Server software, downloads the customizable drug library to the medication delivery pump and receives status or activity information from the pump. Commonly owned U.S. Pat. No. 8,065,161 titled "SYSTEM FOR MAINTAINING DRUG INFORMATION AND COMMUNICATING WITH MEDICATION DELIVERY DEVICES" that issued on Nov. 22, 2011 discloses how the drug library or medical device configuration information is created, edited, stored and communicated to a medication delivery device in the context of a medication management system to deliver substances, such as fluids or fluid medication or both to patients.

According to the above-mentioned commonly owned published patent applications, a typical medication management system includes a point of care computer, such as a barcode point of care computer and/or pharmacy computer, and/or an MMU, in communication with one or more medication delivery devices. The point of care computer(s) and/or the MMU, with associated memory, store and share or communicate various information, such as patient information, prescription information, customized drug library or other information, for managing medication delivery to a patients, such as performing five-rights checking, configuring the medication delivery devices, and receiving and storing event, status or activity information received from the medication delivery devices.

Caregivers and clinicians use outputs from patient monitoring and equipment monitoring devices to make various patient care decisions. Patient monitoring devices and patient care equipment monitoring devices may be connected to a receiver, which receives the output signals from the patient monitoring devices and patient care equipment monitoring devices. In some cases, the receivers may display and/or record the information from the patient and patient care equipment monitoring devices. In other cases, the devices may include a monitor and/or recording medium. The receivers or devices may also have preset or adjustable alarms that are triggered when one of the outputs from the patient or patient care equipment monitoring devices deviates from a pre-set limit.

In hospitals that use infusion pumps and other medical devices, alarms are used to indicate device malfunction, therapy interruptions, end of therapy and other events that need to be handled by the clinical staff. Typically, alarms get displayed on device screens and produce audible sound. In some cases, there are too many devices that alarm in close proximity to each other. As a result, it is very hard to tell which device is actually alarming. The sound of alarms can also disturb or wake up sleeping patients. Hospital nurses usually manage multiple infusions running on multiple patients in one or more given clinical care areas. It is difficult for a nurse to be in the same vicinity of the infusion device at all times during an infusion, thus making it difficult to respond immediately to infusion-related or infusion device alarms. Further, clinical staff is not always in the close proximity to the alarming device to hear the alarm. In such situations it would be desirable for the staff to be notified of device alarms as soon as possible regardless of their proximity to the device so that they can better attend to their patients' needs.

Further, in some patient cases, it is critical to isolate the patient and reduce the exposure of the patient to unnecessary hospital conditions (e.g. burn patient being exposed to drafts or airborne contaminants when opening the door to the patient room). Further, multiple nurses may utilize the same pump on a patient between device cleaning. This results in an increase possibility of contamination due to an increased number of clinicians contacting the device. The pump may be contaminated by a clinician. This contamination may be transferred to the patient either by the clinician that first contaminated the pump or by a subsequent clinician who acquires the contamination by contacting the pump and then who transfers the contamination to the patient in the course of providing care to the patient. Further, contamination applied to a pump may be transferred to other devices and patients by clinicians who come in contact with the contamination on the pump and carry it with them to other pumps and patients where the contamination can be deposited and spread. Where alarms require a clinician to actually come to and contact a pump in order to assess the alarm, shut the alarm off or otherwise respond to the alarm, the likelihood of such contamination and cross-contamination increases.

SUMMARY OF THE INVENTION

A patient care system is disclosed that, in a preferred embodiment, includes at least one medical device such as an infusion pump. Each pump is capable of generating a data message containing information regarding the pump including the status of the therapy being delivered, operating data or both. The patient care system includes an alarm generating system that received the data message from the pump. The alarm generating system assesses the data message from the pump and fires a trigger if certain conditions established by a first set of rules, algorithms or instructions are met. The firing of a trigger produces an alarm message. This alarm message is assessed according to a second set of rules, algorithms or instructions as to whether to suppress the alarm message. For both the first and second algorithms, information generated by each pump is a required input.

The patient care system also includes a dispatching system that is connected to the alarm generating system. The dispatching system is adapted to forward the alarm message to an alarm destination according to a third set of rules, algorithms or instructions. Further, the patient care system includes an alarm destination connected to the dispatching system, the alarm destination expressing an alarm upon receipt by the alarm destination of the alarm.

In an alternate embodiment of the patient care system, the medical device is not part of the patient care system. Instead, the patient care system as disclosed interacts with the medical device. In another alternate embodiment of the patient care system, then alarm destination is not part of the patient care system but instead interacts with the patient care system. In yet another alternate embodiment of the patient care system, both the medical device and alarm destination are not part of the patient care system but instead interact with the patient care system. In yet another embodiment of the patient care system, both including and excluding the medical device and alarm destination or both, the alarm generating system and the dispatching system are combined into a single system.

BRIEF DESCRIPTION OF THE DRAWINGS

FIG. 7 1s a chart of one embodiment of the patient care system showing the process of changing the pump infusion program with a monitor/controlling system.

DETAILED DESCRIPTION OF THE PREFERRED EMBODIMENT

Figure 1:
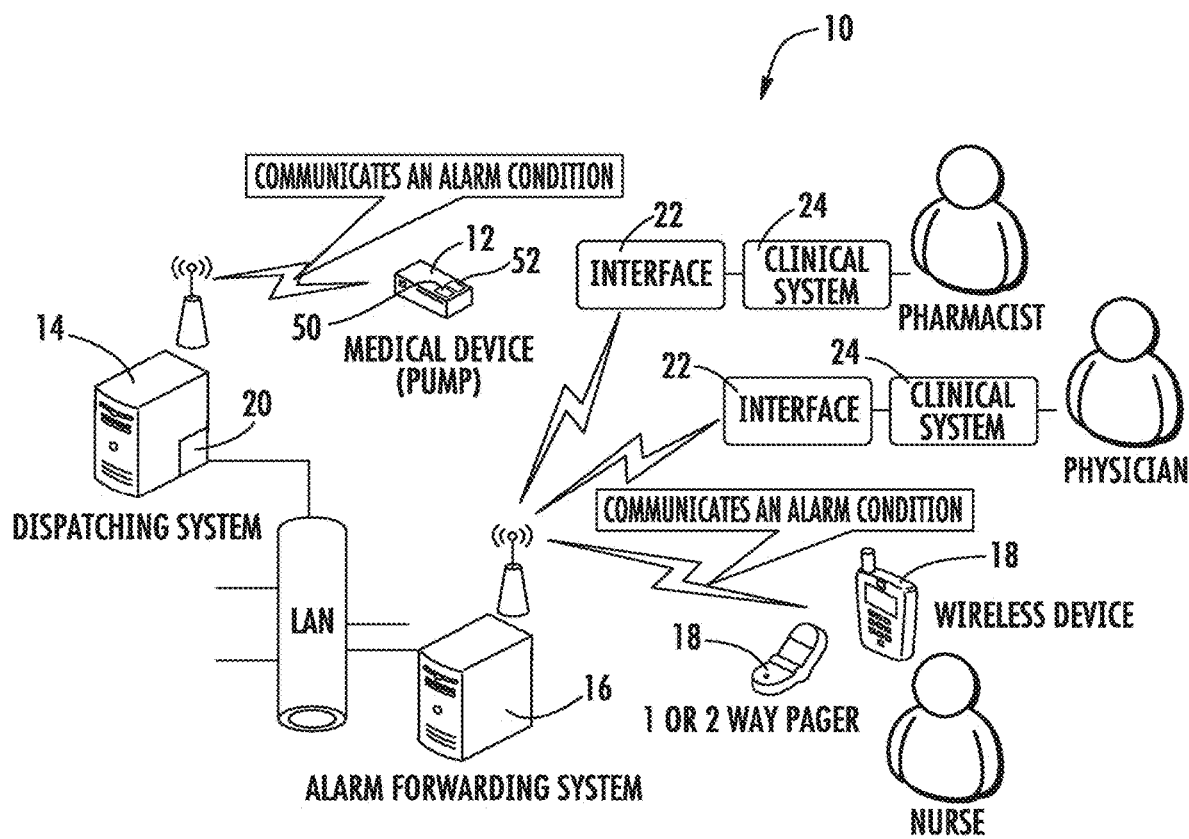
FIG. 1 is a schematic drawing of the architecture of one embodiment of a patient care system.

Referring to the Figures, a patient care system is shown in the Figures generally referred to by the reference number 10. The patient care system 10 interacts with a medical device 12 to manage alarms produced by the medical device 12. The patient care system 10 includes a dispatching system 14, an alarm forwarding system 16 and, in certain embodiments, a monitor/controlling system 18.

The patient care system 10 is intended to be deployed in any hospital or other facility that utilizes medical devices 12, including but not limited to infusion pumps, that are connected to networks either via hardwiring or through wireless connections. Such networks may be specific to the connection of one or more pumps 12 to each other or to control or monitoring devices. The networks may connect many medical devices and allow control or monitoring of a variety of such devices including control or monitoring from and to remote locations.

Medical device 12 is preferably an infusion pump 12 capable of receiving programming data from a nurse or other practitioner. Further, pump 12 is preferably capable of having its operational infusion program reviewed or confirmed or both by the nurse or other practitioner. Examples of pump 12 are the PLUM A+™ infusion system, LIFECARE PCA™ infusion system and SAPPHIRE™ infusion system sold by Hospira, Inc. of Lake Forest, Illinois. Although medical device 12 is preferably an infusion pump 12, pump 12 as applied to the present patient care system 10 is intended to be understood to be any medical pump and more broadly, any medical device that has the capability of producing data and being connectable to a dispatching system 14 as described herein. Each pump 12 or other medical device is capable of generating a data message containing information regarding the pump including the status of the therapy being delivered, operating data or both. Examples of the data message generated by the pump 12 include, but are not limited to, pump 12 status data, the status of the therapy being delivered by the pump 12, event data associated with the pump 12 (e.g., expiration of certain time periods) and alarms associated with pump 12 or the delivery of therapy by the pump 12. Further, in some embodiments, pump 12 includes a local delay timer 50. The local delay timer may be a mechanical timer or a timer implemented in software. The local delay timer 50 is activated and begins counting when an alarm condition message is sent by the pump 12 to the dispatching system 14. In other embodiments of pump 12, pump 12 includes logic 52 that can be either discrete or implemented through software. Logic 52 allows pump 12 to make evaluations or take actions according to programming including rules, algorithms or instructions implemented on or associated with the logic 52 and may, in certain embodiments, also provide the local delay timer 50.

Dispatching system 14 is preferably a network application that manages alarms and preferably includes a dispatching server 20 capable of running software. A key function of the dispatching system 14 is to facilitate alarm management from the pump 12 to one of more alarm destinations (e.g., monitor/controlling systems 18) and back. For example, in a preferred embodiment, the dispatching system 14 is adapted to forward the alarm messages from the pump 12 to one or more monitor/controlling systems 18 according to a set of rules, algorithms or instructions. In a preferred embodiment of the patient care system 10, these rules, algorithms or instructions are executed on the alarm forwarding system 16 which, in effect, orchestrates the alarm flow from the pump 12 to one or more monitor/controlling systems 18 and back in order to implement safe, secure and reliable alarm handling. In a variant of this embodiment, rules, algorithms or instructions may be implemented on the pump 12 itself. The rules, algorithms or instructions can be configured by a rule editor.

In one embodiment, the dispatching server 14 incorporates an alarm forwarding system 16 that separates the alarm communication from the actual means of communication and forwards alarm information to monitor/controlling systems 18 according to rules, algorithms or instructions. The alarm forwarding system 16 assesses data messages produced by the pump 12 that are passed from the pump 12 to the alarm forwarding system 16 by the dispatching system 14 and fires a trigger if certain conditions established by a first set of rules, algorithms or instructions are met. The firing of a trigger produces an alarm message that is assessed according to a second set of rules, algorithms or instructions as to whether to suppress the alarm message. An example of a dispatching server 14 is a server equipped with the Hospira MedNet™ medication management software manufactured and sold by Hospira, Inc. of Lake Forest, Illinois. The dispatching server can be used in combination with a hospital's existing alarm forwarding system or can be used in combination with a hospital's alarm forwarding system that has been modified to interface with the alarm messages received from dispatching server 14. In a preferred embodiment of the patient care system 10, the dispatching system 14 and alarm forwarding system 16 are separate systems that are connected together, for example, by a local area network (LAN) or wide area network (WAN), whether wireless, hardwired or connected by optical fibers, or any other communication protocol or system. However, the dispatching system 14 and alarm forwarding system 16 can be combined into a single system that performs the functions of the dispatching system 14 and alarm forwarding system 16 as described herein.

The patient care system 10, in a preferred embodiment, includes one or more monitor/controlling systems 18 connected to the dispatching system 14. The function of the monitor/controlling system 18 is to connect to the dispatching system 14, receive alarms and data from the dispatching system 14, communicate such alarms and data to a clinician and, in some embodiments, allow a clinician to produce a response to such alarms and data and otherwise produce acknowledgment or control responses and communicate such responses and acknowledgments to the dispatching system 14. The monitor/controlling system 18 preferably expresses an alarm upon receipt by the monitor/controlling system 18 of an alarm notification. The alarm can take various forms, including but not limited to an audible, visual, or vibratory alarm. The list of possible monitor/controlling systems 18 includes, but is not limited to, mobile wireless devices, network connected workstations, laptop computers, tablets, electronic mail, text messages, pagers and even fax machines In an embodiment of the patient care system 10, medical device 12 forwards a data message to dispatching system 14, and dispatching system 14 accesses the data message to determine if an alarm condition is met and if an escalated alarm should be suppressed. For example, a local alarm at the medical device 12 could be temporarily suppressed while an alarm is sent to a remote monitor/controlling system 18. The content of the data message could be a required input for the evaluation of both whether or not an alarm condition is met, and if the escalated alarm should be suppressed. As mentioned above, the data message could contain information regarding pump therapy status data, pump operating point data, or both pump therapy status data and pump operating point data. If an alarm condition is met, dispatching system 14 could cause alarm forwarding system 16 to forward an alarm message to one or more monitor/control systems 18. As a result, the monitor/controlling system 18 does not sound the alarm at the monitor/controlling system 18 except under certain predetermined conditions. Further, the medical device 12 itself may not sound an alarm except according to certain predetermined conditions.

Figure 2:
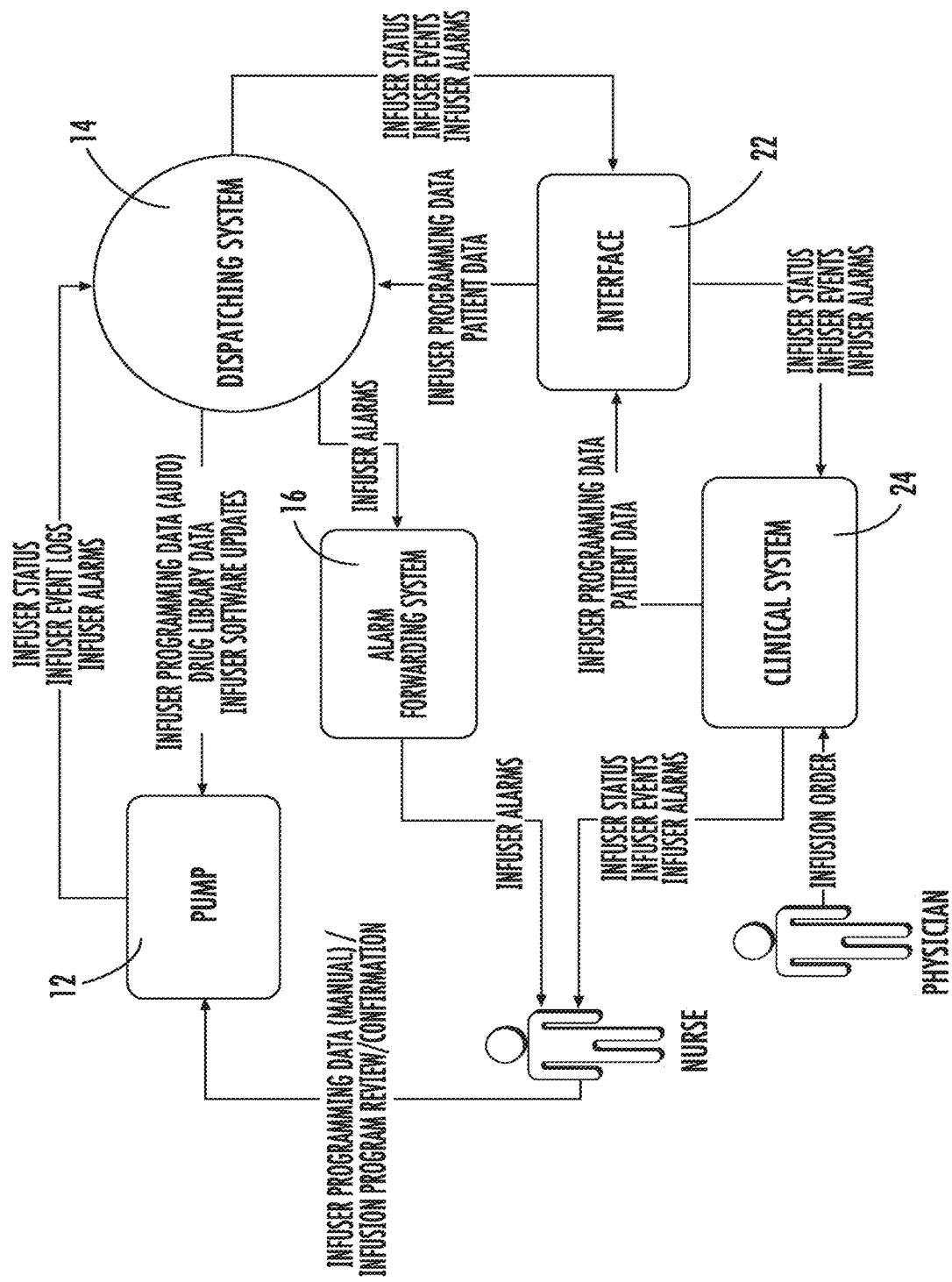
FIG. 2 is a data flow chart of one embodiment of a patient care system.

FIG. 2 shows an alarm condition being sent to the nurse and pharmacist to aid in their workflow (e.g., the nurse will pick up the next package of medication from the pharmacist and the pharmacist is informed that the infusion is nearing completion, which is the cue to prepare for the nurse to come and get the next package of medication for infusion). As can be seen in the embodiment shown in FIG. 2, pump 12 is in communication with the dispatching system 14 so that pump 12 sends status data about pump 12 to the dispatching system 14. Such status data includes, but is not limited to, patient biometric, physiological or medical parameter information, the location of pump 12 and the type and amount of medication administered by the pump 12. In addition, pump 12 sends event data to the dispatching system 14. Such event data includes, but is not limited to, information indicating that the infusion is nearing completion. Further, pump 12 sends alarm data to the dispatching system 14. Alarm data, as used in this specification, means all notifications that can benefit physicians, clinical staff or patients in handling the operation and safety of the pump 12.

Although the patient care system 10 described herein interacts with one or more pumps 12, the pumps 12 are not required to be part of the patient care system 10. However, as described hereafter, various aspects of the functionality of the patient care system 10 may be shared with the pump 12 so that in some embodiments the pump 12 may be part of the patient care system 10.

Besides receiving data from a pump 12, the dispatching system 14 may also send programming data to the pump 12. Such programming data may reconfigure the parameters and operation of the pump 12 with respect to both infusing of medication by the pump 12 and the type, amount and frequency of data gathered by the pump 12 and sent to the dispatching system 14. Further, dispatching system 14 may also send drug library data to the pump 12 which may then be used by pump 12 to configure limits and infuser settings to be used in the infusion of medication to the patient. In addition, the dispatching system 14 may send software updates to the pump 12 so that pump 12 has the most current software for its operations.

Dispatching system 14 interacts with alarm forwarding system 16 to forward alarms generated by the dispatching system 14 according to the appropriate recipient according to rules, algorithms or instructions. These rules, algorithms or instructions can, in part, be based on or take into consideration the clinical care area (CCA), patient identification, alarm priority, location of the pump 12 and the type of drug being infused by the pump 12. The rules, algorithms or instructions can be fixed and predetermined or can be customizable by the hospital or healthcare facility according to their own preferred practice or other practices recommended by others. An example of an appropriate recipient is the nurse who is caring for a patient that is receiving therapy from a pump 12. Further, where the alarms are sent to appropriate recipients, who that recipient is or the location where the alarm was forwarded may also be indicated or displayed on the pump 12 itself.

Dispatching system 14 may also communicate data, raw or processed by the dispatching system 14, to a clinical system 24 through an interface 22. Interface 22 provides a connection between the dispatching system 14 and a clinical system 24. The clinical system 24 may be another network (separate or interconnected with the network of dispatching system 14) where such network communicates information to the appropriate recipients such as the nurse having supervisory responsibility for the nurse caring for a patient that is receiving therapy from a pump 12, a physician overseeing the care of the patient, a pharmacist preparing medication for the patient or any combination of these or others having a need to know the status of the infusion therapy being applied to a patient through a pump 12. Examples of the data that can be communicated from the dispatching system 14 to and from the clinical system 24 via the interface 22 and from the clinical system 24 to an appropriate recipient includes, but is not limited to, the raw data produced by the pump 12 such as pump status data, pump event data and alarms associated with pump 12 or rules, results and data that has been processed by the dispatching system 14 or alarm forwarding system 16.

Further, the clinical system 24 allows appropriate personnel, such as the physician overseeing the care of the patient, to interface with and ultimately control or change the operation of the pump 12. For example, a physician through the clinical system 24 could modify the infusion parameters of the pump 12 by sending an infusion order to the clinical system 24 that passes through the interface 22, dispatching system 14 and ultimately to the pump 12. Further, new or modified programming data for the pump 12 may be entered into the clinical system 24, passed through the interface 22 to the dispatching system 14 and ultimately to the pump 12 where the current programming of pump 12 is either modified or replaced, preferably in an automated and/or remote manner.

Interface 22 likewise allows appropriate personnel to administer the rules used to control alarm forwarding in the system via a rule editor available on monitor/control device 18 or clinical system 24. The administration interface would allow the hospital personnel to determine rules for what contents from a data message from pump 12 would cause an alarm message to be generated. For example, an administrator could determine that an alarm would be generated whenever a certain kind of medication was interrupted, even if only temporarily, while the interruption of a different kind of medication did not generate an alarm unless the interruption was of a sufficient duration. The administration interface could also allow the hospital personnel to determine rules for what contents from a data message from pump 12 would control how and if certain alarm messages would be suppressed. For example, an administrator could determine that an alarm message generated based on a data message regarding a life critical or otherwise high risk drug, such as analgesics, sedatives or anticoagulants like Heparin for example, would not be suppressed at all, an alarm message generated based on a data message regarding a less critical drug could be locally suppressed at the device but could not be cleared remotely, and an alarm message generated based on a data message regarding a noncritical drug could be both locally suppressed at the device and cleared remotely.

Figure 3:
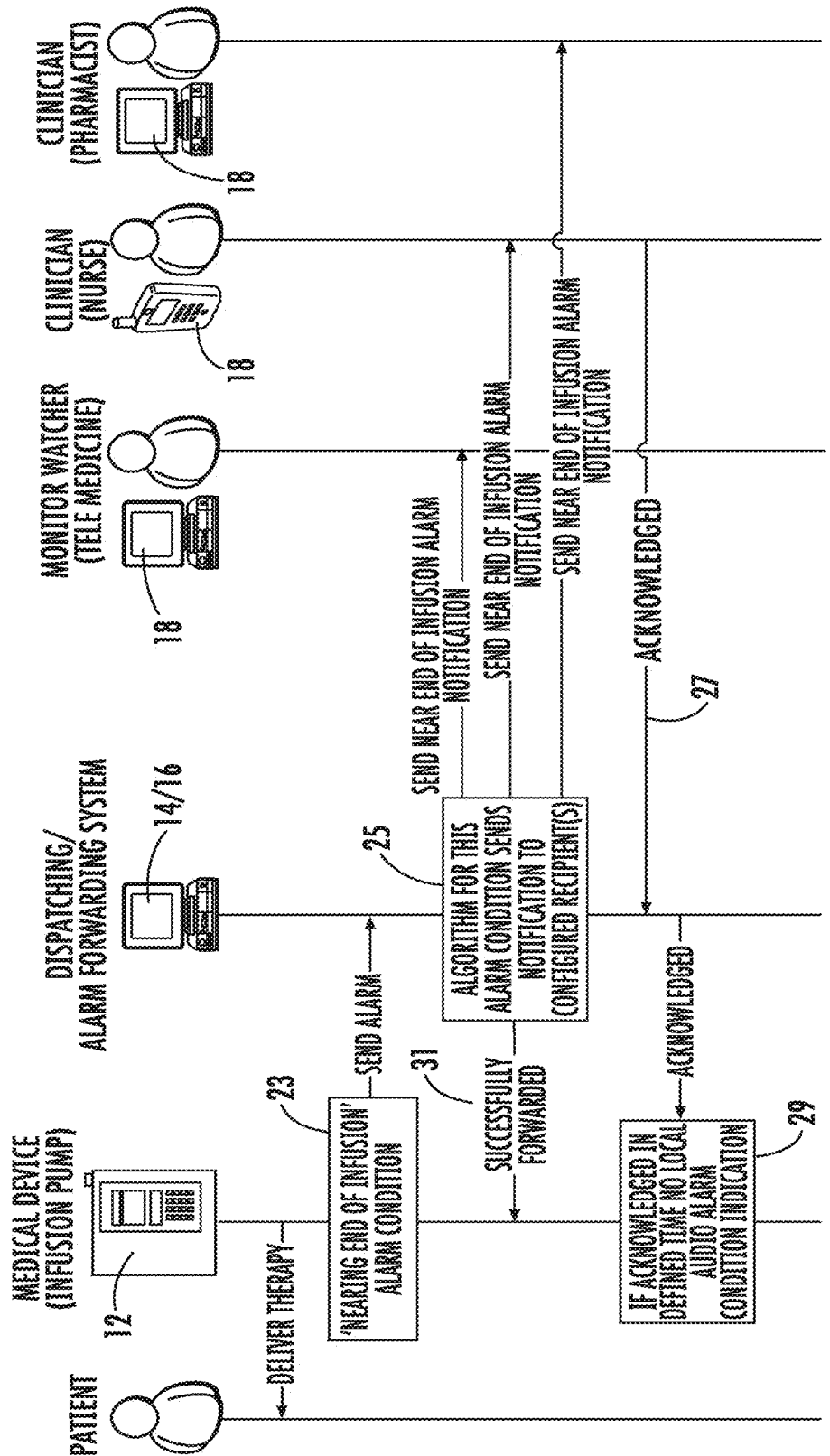
FIG. 3 is a chart showing the flow of information between various personnel and components of the patient care system of FIG. 1.

An example of how information flows in patient care system 10 can be described with references to FIG. 3. The main communication nodes in FIG. 3 include pump 12, dispatching system 14, alarm forwarding system 16, alarm destinations or monitor/controlling systems 18, the patient, nurse, telemedicine personnel, and pharmacist. As can be seen, an exemplary alarm condition 23, "Nearing the End of Infusion," is communicated from the pump 12 to the dispatching system 14. The dispatching system 14, operating according to an algorithm 25 for this alarm condition, sends the "Nearing the End of Infusion" alarm 23 to the alarm forwarding system 16, which broadcasts, according to its rules or algorithms 25 to the monitor/controlling system 18 and clinical system 24 through the interface 22 (FIG. 2). Alternatively or in addition, the dispatching system 14 can send the alarm 23 to the interface 22 where it is subsequently passed to the clinical system 24 where it passes to the appropriate personnel such as the nurse, pharmacist or physician. In this way, multiple alarm messages are sent in parallel to the appropriate personnel according to the operation of the algorithm 25 operating on the dispatching system 14. Further, in a variant of this embodiment, an initial alarm message may be forwarded from a recipient of such alarm message to another person not initially sent the alarm message in a so-called "serial forwarding" fashion. Further, to avoid the same alarm being received by multiple devices at different times, which could give the mistaken impression that there are more alarms than there actual are, alarm messages can be synchronized when dispatched to multiple recipients (e.g., various monitor/controlling systems 18 such as a mobile tablet and a nurse station) so that the alarm messages arrive at the same time.

The administration interface could also be used to control how certain alarm messages flowed in patient care system 10. For example, the rules applied to alarm messages by alarm forwarding system 16 could be configurable so that alarm messages pertaining to life critical drugs were forwarded to various monitor/controlling systems 18 in parallel while alarm messages pertaining to less critical drugs were forwarded to a single monitoring system 18 and serially forwarded to another monitoring system 18 only in the event that the alarm was not acknowledged.

As can also be seen, the dispatching system 14 may receive an acknowledgment message 27 from the appropriate personnel, in this case, the nurse. Upon receipt of an alarm message, the nurse may send an acknowledgment message acknowledging receipt of the alarm message. Once again, the rules, algorithms or instructions 25 operating on dispatching system 14 for this alarm condition processes the acknowledgment and determines if additional action needs to be taken. For example, if an acknowledgment message is not received within a predetermined time, the algorithm could instruct the pump 12 to issue a local alarm to alert those caring for the patient in the vicinity of the patient of this alarm condition. Of course, if the alarm condition is acknowledged before the predetermined time has expired 29, no such local alarm may be required as defined by the algorithm 25 and thus no local alarm will sound by pump 12.

In embodiments of patient care system 10 where an alarm condition has been forwarded to the dispatching system 14, it is desirable, but not required, to indicate on the pump 12 that an alarm occurred and that it has been forwarded. Further, in situations where the local alarm is suppressed, it is desirable, but not required, that the time remaining before the alarm sounds or is otherwise indicated locally on the pump 12 be displayed so that the clinician located in the vicinity of pump 12 may see and act upon this information appropriately.

Figure 4:
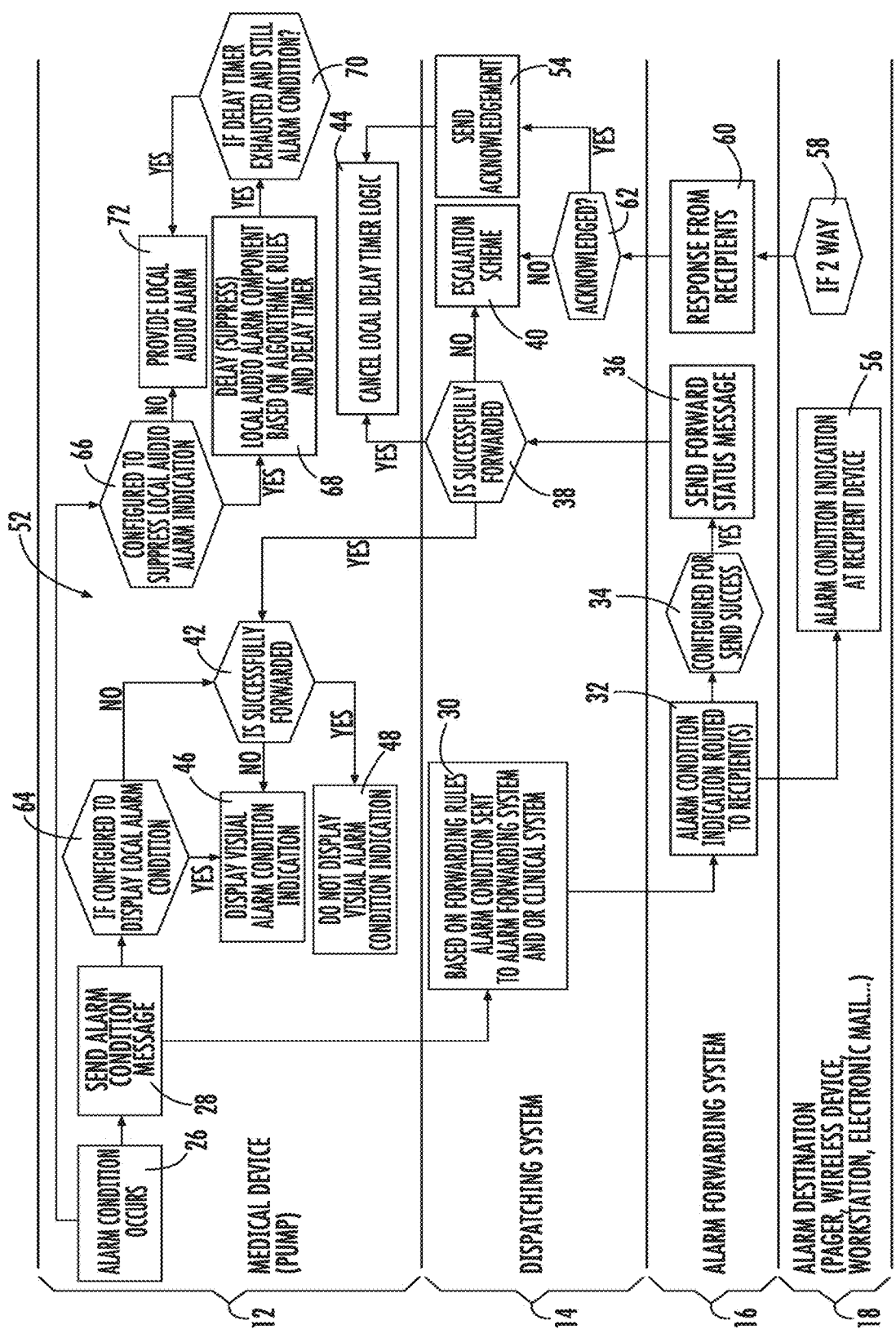
FIG. 4 is a flow chart of one embodiment of the patient care system of FIG. 1.

Further, a desirable function of the patient care system 10 is the capability to have confirmation that an alarm has been successfully delivered. As shown in FIGS. 3 and 4, the algorithm 25 running on dispatching system 14 could, if so defined, send a "successfully forwarded" message 31 back to the pump 12 after alarm messages have been sent to the appropriate personnel by the dispatching system 14 as described above. This "successfully forwarded" message 31 could be processed by the rules, algorithms or instructions 25 on dispatching system 14, alarm forwarding system 16 or pump 12 software and rules, algorithms or instructions to take action as defined by such software and rules, algorithms or instructions. For example, beyond just delivering such a "successfully forwarded" message 31 to the pump 12, the "successfully forwarded" message 31 may be displayed, including by activation of an audible, visual or tactile messaging systems as described herein to alert an appropriate caregiver of such receipt.

Each combination of alarm forwarding, acknowledgment, and particular kinds of suppression can be referred to as a suppression protocol. For example, the combination of suppressing a local auditory alarm until either a set time has elapsed or an alarm forwarding confirmation or acknowledgment was received is a first suppression protocol, while the combination of suppressing a remote alarm to a supervisor until either a set time has elapsed or a primary care giver cleared an alarm locally at the medical device is a second suppression protocol. Various suppression protocols can be created by hospital personnel via use of the rules editor mentioned previously, which can in one embodiment be incorporated into the Hospira MedNet™ software. The various suppression protocols can further be selectively applied by the care system based on the content of medical device data messages, alarm messages, and other information available to the system. As such, particularly stringent suppression protocols can be applied to low priority alarms automatically while more lax suppression protocols are applied to higher priority alarms.

In all of the above situations in which the content of a data message from pump 12 or the content of an alarm message were used to control the manner in which an alarm was generated, suppressed, or forwarded, the clinical care area (CCA) of the pump or medical device 12 can be used additionally or in the alternative as an input to a rule or can be used to select which rule should to be applied. This functionality provides significant benefits in that an alarm forwarding protocol or alarm suppression protocol might be appropriate for a given medical situation in one CCA and not appropriate in another. For example, the temporary interruption of a basic saline drip may be a low priority alarm towards which a stringent suppression protocol is applied in one CCA while the same medical event is a high priority in a level 4 NICU where the slightest divergence from a planned treatment can be more problematic for the patient. The CCA can be received as an input for any of these determinations by first being programmed into the medical device when it is deployed or provided in a drug library downloaded to the medical device, and subsequently selected by the clinician on the device so that the selected CCA information is delivered as part of the data message generated by the medical device 12. In the alternative, the CCA can be determined indirectly from the data message and/or alarm message by conducting a lookup operation on a database associated with a server that is in communication with a plurality of the medical devices in the healthcare facility. For example, an ID number associated with a pump could be received in a data message and then applied to a database to lookup the CCA area in which the pump had last been deployed, programmed in, or heard from via the network.

FIG. 4 shows the operation of one possible function of the patient care system 10. In this function, the dispatching system 14 and alarm forwarding system 16 are shown as separate systems. But, as described above, it is intended to be within the scope of the invention that the dispatching system 14 and alarm forwarding system 16 be combined into a single system or software module that performs the functions of the dispatching system 14 and alarm forwarding system 16 as described herein. Further, as can be seen in FIG. 4, the medical pump 12 itself may operate according to certain algorithms and may itself perform some of the functionality of the dispatching system 14 and alarm forwarding system 16.

In this example, if an alarm condition occurs at 26, the pump 12 generates an alarm condition message at 28. This alarm condition message is sent from pump 12 to the dispatching system 14 where the alarm condition message is evaluated at 30. The alarm condition message preferably includes information relevant to the alarm such as pump 12 ID, the patient ID/name, location of pump 12 and type/concentration/name of drug used. Pump 12 gets acknowledgement from the server of the dispatching system 14 that it received the alarm and acknowledgement from the forwarding system 16 and/or the alarm destination or recipient entity.

The evaluation at 30 occurs according to rules, algorithms or instructions established in the dispatching system 14. If, at step 30, it is determined that the alarm condition received from pump 12 should be passed to the alarm forwarding system 16 to be managed, the alarm condition is passed to the alarm forwarding system 16 where it is received at step 32. Alarm forwarding system 16 then forwards the alarm condition to the appropriate personnel via monitor/controlling systems 18 according to the rules, algorithms or instructions established in alarm forwarding system 16 for that particular alarm condition. Alarms have different priorities and repeat rates and require different responses. As a result, the rules, algorithms or instructions established in alarm forwarding system 16 determine which alarms get priority when one or more alarms are present at the same time as well as the appropriate routing, timing and display of alarm information in alarm conflicts. Further, the rules, algorithms or instructions established in alarm forwarding system 16 determine how, when and by whom alarms may be cancelled or suppressed, particularly in alarm conflict situations.

The monitor/controlling system 18 to which the alarm forwarding system 16 forwards the alarm condition may be any of a number of devices such as a pager, mobile phone, wireless device, tablet, workstation, email or any other form of communication that is able to communicate with the alarm forwarding system 16 and communicate information to the appropriate personnel. In the embodiment shown, the dispatching system 14 itself evaluates, according to rules, algorithms or instructions established in the dispatching system 14, whether the alarm condition received from pump 12 should be passed to the alarm forwarding system 16 to be managed. In an alternate embodiment, the dispatching system 14 contains no such evaluation system but instead passes the alarm message directly to the alarm forwarding system 16.

Upon receipt of an alarm condition message by the alarm forwarding system 16 at 32, in the embodiment shown, the program passes to step 34 where it is determined whether the alarm forwarding system 16 is configured to send a "successfully received" acknowledgment of the alarm condition message. If the alarm forwarding system 16 is so configured, the program passes from step 34 to step 36 where a "successfully received" acknowledgment message is generated and sent from the alarm forwarding system 16 to the dispatching system 14.

The "successfully received" message sent from alarm forwarding system 16 is received at the dispatching system 14 at step 38. Step 38 determines whether the alarm condition message originally generated by pump 12 and passed to dispatching system 14 was successfully forwarded to the alarm forwarding system 16. If, according to the logical operations of this step 38, the alarm condition message was not received by the alarm forwarding system 16, the program passes to step 40 where an escalation scheme is entered. The escalation scheme includes a determination, by rules, algorithms or instructions, of the appropriate response when an alarm condition message has not been acknowledged. Examples of such an appropriate response could be resending the alarm condition message, sending the alarm condition message to another monitor/controlling system 18, triggering a local display of the alarm condition on the pump 12, causing the display of an alarm alert condition at some other device, or any other appropriate response as determined by those having care of the patient and which have been programmed into the rules, algorithms or instructions operating on the dispatching system 14.

If the alarm condition message generated by pump 12 was ultimately received by the alarm forwarding system 16, then at step 38 a confirmation message is automatically sent to both steps 42 and 44 which are processed on the pump 12 by the operation of the logic 52 as explained above. At step 42, whether the alarm condition message was successfully forwarded to alarm forwarding system 16 is evaluated. If the alarm condition message was not successfully forwarded to the alarm forwarding system 16, the program passes to step 46 where a local alarm is visually displayed. If however, it is ascertained at step 42 that the alarm condition was successfully received by the alarm forwarding system 16, the program passes to step 48 where no local alarm is displayed by pump 12.

In this embodiment, pump 12 includes a local delay timer 50 as described above. Such a local delay timer 50 is activated when an alarm condition message is sent at step 28 by the pump 12 to the dispatching system 14. As mentioned, at step 38 the dispatching system 14 determines whether the alarm condition message generated by pump 12 was received by the alarm forwarding system 16. If the alarm condition message was ultimately received by the alarm forwarding system 16, the program also passes to step 44. Step 44 determines whether to cause the local delay timer 50 to cease. This determination at step 44 occurs according to rules, algorithms or instructions. In particular, this determination preferably takes into consideration whether an acknowledgment of receipt of an alarm message 54 has been sent by medical personnel at 58 and ultimately passed through steps 60 and 62 to step 54 where an acknowledgment message is sent from step 54 to step 44. Logic 52 (FIG. 1 or general arrow in FIG. 4) within pump 12 is set up to send a local alarm message if the local delay timer 50 (FIG. 1) exceeds its allotted time and preferably under the rules, algorithms and rules governing step 44, where no acknowledgment of an alarm condition message is received from the dispatching system 14 via step 54. However, upon receipt of an acknowledgement of an alarm condition message from the dispatching system 14 at 54, the local delay timer 50 ceases counting and no local alarm message is generated. The length of the delay set in the local delay timer 50 can be set, for example, according to the priority of the type of alarm 28 generated or the type/concentration/name of drug being infused by the pump 12. Further, if receipt of an acknowledgement of an alarm condition message arrives from step 54 after the timeout of the local delay timer 50, and as a result a local alarm has already started, according to rules, algorithms or instructions, the patient care system 10 can stop the local alarm, restart the local delay timer 50 or both.

Receipt at the monitor/controlling system 18 of an alarm condition causes the monitor/controlling system 18 to display the alarm condition at 56. This display may take the form of visual, audible or tactile displays. For example, the display may cause an audible alarm to sound indicating to the clinician the receipt of an alarm condition message. Further, the display may, on a viewing screen, display information related to the alarm condition message. In addition, the display may include activation of a visual indicator of the receipt of an alarm condition message such as a flashing light. Finally, the display may take the form of a tactile display such as a vibrating device indicating to the clinician the receipt of an alarm condition message. This list of possible displays is intended to illustrate possible displays or indications that a monitor/controlling system 18 may use. However, it is to be understood that this list is illustrative and not intended to be limiting. As a result, it is intended that any type of display that attracts the attention of the clinician to the receipt of an alarm condition message or displays or otherwise communicates the contents of an alarm condition message is intended to be within the scope of the present patient care system 10.

Upon receipt of an alarm condition message by a monitor/controlling system 18, the clinician may send an "acknowledgment of receipt" message back to the dispatching system 14 if their destination device permits two-way communication. Generating and sending such an acknowledgment message occurs at the monitor/controlling system 18 at 58. The acknowledgment receipt message is sent from the monitor/controlling system 18 to the alarm forwarding system 16 at 60 where the acknowledgment of the receipt of the alarm condition message is passed to the dispatching system 14 at 62. Step 62 determines whether the alarm message 28 previously sent from the dispatching system 14 has been acknowledged. If it has not, the program passes to 40 where an escalation scheme is determined according to rules, algorithms or instructions.

If, at step 62, it has been determined that an alarm condition acknowledgment message has been received, the program passes to step 54 where acknowledgment message is sent from the dispatching system 14 to the pump 12 at 44. This alarm condition 28 is evaluated at 64 to determine, according to rules, algorithms or instructions, if this alarm condition requires the display of a local alarm on pump 12. Whether such an alarm condition 28 requires the display of a local alarm on pump 12 is determined according to certain rules, algorithms or instructions that have been programmed into the pump 12. If the alarm condition 28 requires that a local alarm be displayed on pump 12, such an alarm is displayed at 46. If the alarm condition 28 does not require that a local alarm be displayed, the program advances to 42 where it is evaluated whether the alarm condition was successfully forwarded to appropriate personnel through the dispatching system 14 and alarm forwarding system 16.

The creation of an alarm condition at 26, in addition to the sending of an alarm condition message at step 28, also causes the program operating according to the logic 52 on pump 12 to move to step 66 where it is determined, according to rules, algorithms or instructions, whether pump 12 is configured to suppress the local alarm audio alarm.

Determining whether pump 12 is configured to express the local alarm audio alarm is done according to rules, algorithms or instructions programmed on the pump 12.

If, at step 66, it is determined, according to rules, algorithms or instructions, that the pump 12 is configured to suppress the local audio alarm, the program advances to step 68 where it is evaluated whether to delay or suppress the local audio alarm based on its rules, algorithms or instructions including, but not limited to, reference to the current stage of the local delay timer 50. If, at step 68, it is determined that the local audio alarm should be suppressed, the program passes to step 70. Step 70 determines whether the local delay timer 50 has exhausted its predetermined delay time and the alarm condition still persists. If the local delay timer 50 has exhausted its local delay time and the alarm condition still persists, the program passes to step 72 where pump 12 provides a local audio alarm even though the alarm had previously been determined to be suppressed. The reason the alarm suppression is overridden in this embodiment is that the failure to receive an acknowledgment of receipt of an alarm notice, as evidenced by the local delay time 50 timing out, has been determined, according to rules, algorithms or instructions, to require an alarm to be generated. Also, according to rules, algorithms or instructions, the alarm can be generated immediately or can be generated after taking further action (e.g., resending the alarm message to see if an acknowledgment or receipt of the alarm message returns). If at step 66 it is determined that pump 12 is not configured to suppress a local audio alarm indication, the program passes to step 72 where pump 12 provides a local audio alarm. Either or both a local audio or visual alarm can be produced at 46 and 72.

Although embodiments of the patient care system 10 discussed above had the alarm forwarding system 16 sending a "successfully received" acknowledgment of the alarm condition message, this is not required for the patient care system 10. Further, although those embodiments of the patient care system 10 had an escalation scheme 40, that also is not required for the patient care system 10. Similarly, various explicit acts, evaluations, messages sent or suppressed, alarms activated or suppressed and similar aspect of the embodiment described above and with respect to other embodiments shown may be eliminated or added in a wide variety of permutations and combinations and still fall within the scope of the invention. Patient care system 10 allows for the management of alarms in all varieties of the term "management." The various aspects of "managing" alarms given in this description are intended to be illustrative and not limiting.

Figure 5:
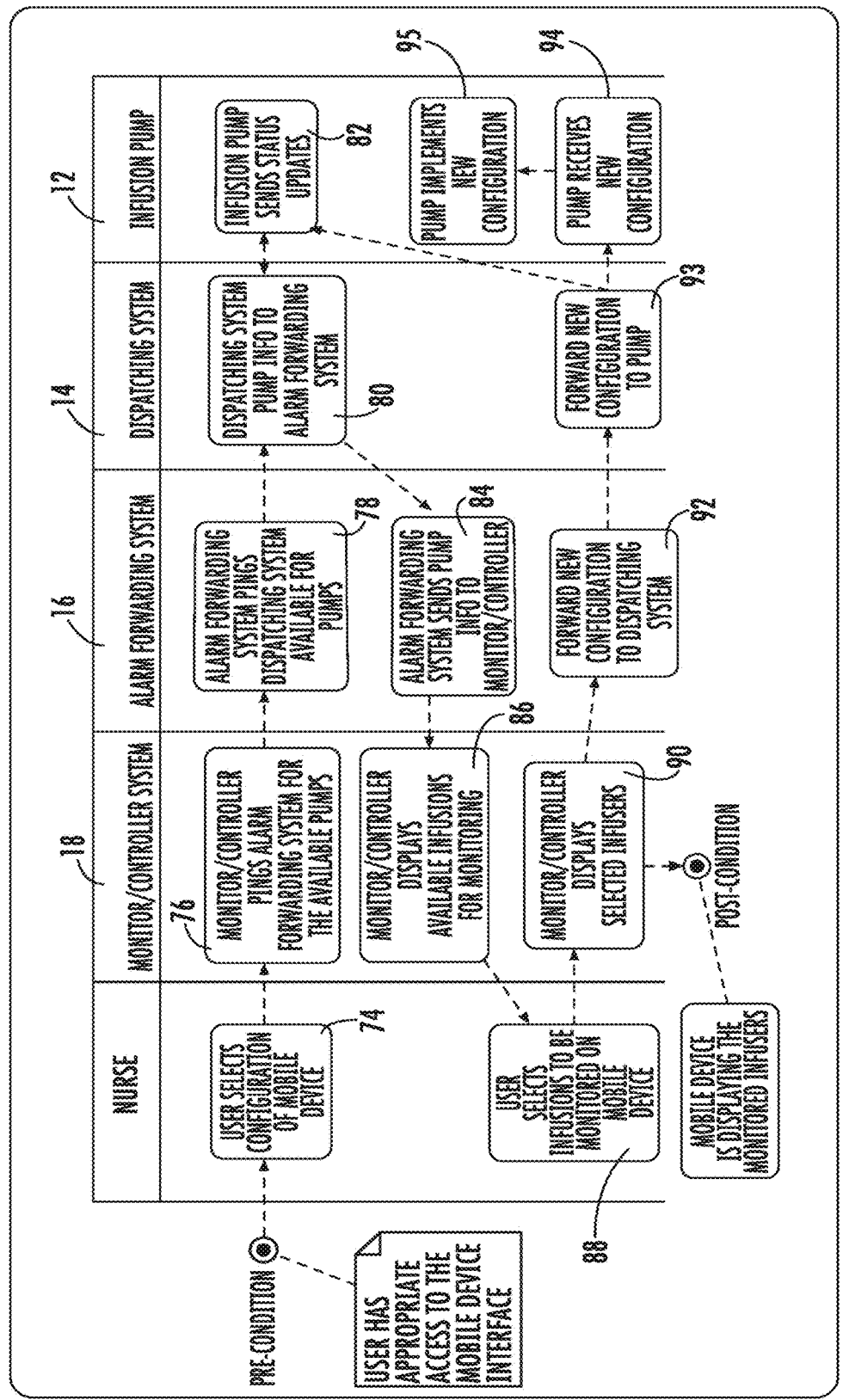
FIG. 5 is a chart of one embodiment of patient care system showing the process of configuring a pump from a monitor/controlling system.

FIG. 5 indicates the interrelationship between an administrator, such as an information technology (IT) specialist, a biomedical engineer, or a nurse or other clinician with responsibility for care of a patient, with the pump 12 through dispatching system 14, alarm forwarding system 16, and monitor/controlling system 18. Where the administrator desires to configure the pump 12 at 74, the administrator sends a command through the monitor/controller system 18 at 76.

Where an administrator desires to reconfigure a pump 12, the monitor/controller system 18 "pings" the alarm forwarding system 16 at 78 to determine which pumps 12 are available for configuration. The alarm forwarding system 16 then "pings" the dispatching system 14 at 80 to determine which pumps 12 are available for configuration. The pumps 12 in communication with dispatching system 14 send their identification information and data to dispatching system 14 at 82. This can be a near real time push of data from the pumps 12 to the dispatching system 14 or the data can be pulled in response to a request or "ping" of the pumps by the dispatching system 14. Dispatching system 14 then sends information about the available pumps 12 to the alarm forwarding system 16 10 at 84 where such information is sent to the monitor/controller system 18 at 86 where the monitor/controller 18 displays the relevant information about this particular pump 12 including the current status of the pump and the range of available options for reconfiguration. By monitor/controlling system 18 displaying this information, the information is made available to the administrator.

Once the administrator has determined which pumps 12 are available for configuration, the administrator selects the pump 12 to be configured at 88. The administrator makes the desired selection on the monitor/controller system 18 which then displays the newly configured settings about this particular pump 12 at 90. Once the administrator has entered the particular parameters for configuration of the desired pump 12 on the monitor/controlling system 18, the monitor/controller system 18 passes this information to the alarm forwarding system 16 at 92 which sends the information to the dispatching system 14 at 93 where the parameters configuration are sent to the selected pump 12 by the dispatching system 14 where they are received by the pump 12 at 94 and implemented on the pump 12 at 95.

A similar process is employed for the administrator to configure the dispatching system 14, alarm forwarding system 16 or the monitor/controller system 18 itself. If the monitor/controller system 18 itself is to be configured, the configuration can take place directly by entering the new configurations on the monitor/controlling system 18. However, it may be desirable to alert others through the dispatching system 14 or clinical system 24 of such configuration changes. In that case, the monitor/controller system 18 sends the configuration information to the alarm forwarding system 16 which sends this information to the dispatching system 14 which then sends the information, according to rules, algorithms or instructions on the dispatching system 14, to the appropriate locations.

Where the alarm forwarding system 16 1s to receive new configurations, configurable aspects of the alarm forwarding system 16 are displayed on the monitor/controller system 18. The desired configurations for the alarm forwarding system 16 are entered into the monitor/controlling system 18 which then sends the new configurations to the alarm forwarding system 16 to be implemented. Again, it may be desirable to alert others through the dispatching system 14 or clinical system 24 of such configuration changes. In that case, the alarm forwarding system 16 sends the configuration information to the dispatching system 14 which then sends the information, according to rules, algorithms or instructions on the dispatching system 14, to the appropriate locations.

Where the dispatching system 14 is to receive new configurations, configurable aspects of the dispatching system 14 and alarm forwarding system 16 are received from the dispatching system 14, passed through the alarm forwarding system and displayed on the monitor/controller system 18. The desired configurations for the dispatching system 14 are entered into the monitor/controlling system 18 which then sends the new configurations to be implemented by the dispatching system 14. Again, it may be desirable to alert others through the dispatching system 14 or clinical system 24 of such configuration changes. In that case, the dispatching system 14 sends the information, according to rules, algorithms or instructions on the dispatching system 14, to the appropriate locations.

In this embodiment, the interface 22 and clinical system 24 are not explicitly shown. However, the interface 22 and clinical system 24 may be incorporated into a monitor/controller system 18. However, it is to be understood that interface 22 and clinical system 24 may be separate and independent systems or that the functions of interface 22 and clinical system 24, in whole or in part, may be performed by the dispatching system 14, alarm forwarding system 16 or monitor/controlling system 18. Further, it is within the scope of the patient care system 10 that the function or elements or both of the dispatching system 14, alarm forwarding system 16, interface 22, clinical system 14 and monitor/controlling system 18 be combined in any permutation or combination of such functions or elements including into a single system.

Figure 6:
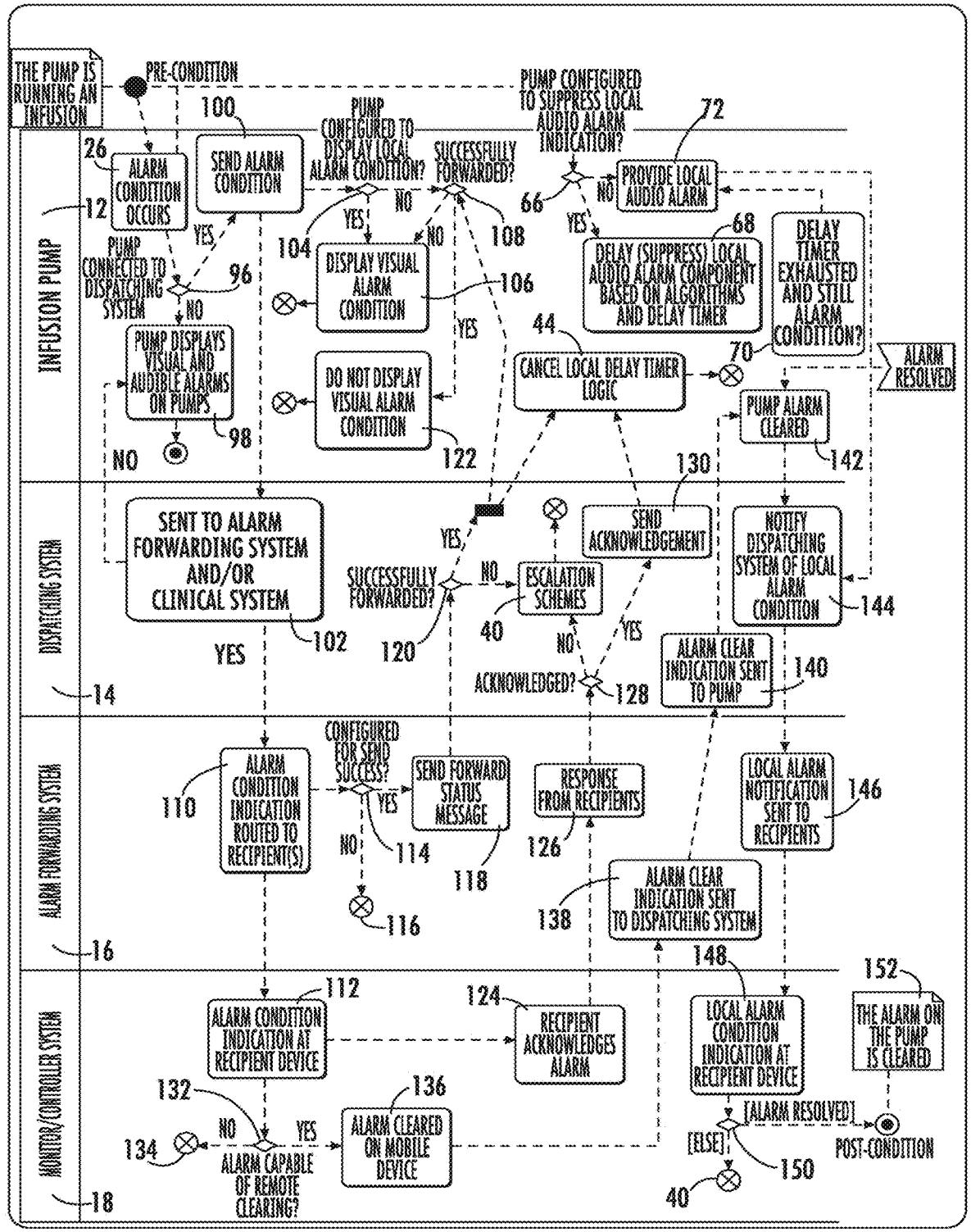
FIG. 6 is a flow chart of one embodiment of patient care system showing the alarm forwarding and acknowledgment functions.

The operation of the patient care system 10 with respect to the alarm forwarding function is shown in FIG. 6. When an alarm condition occurs at 26, pump 12 determines at 96 whether pump 12 is connected to the dispatching system 14. If pump 12 is not connected to the dispatching system 14, the program passes to step 98 where the pump displays a visual or audible alarm or both on pump 12 indicating that pump 12 is not connected to the dispatching system 14. If, at step 96, it is determined that the pump 12 is connected to the dispatching system 14, the program passes to step 100. At step 100, pump 12 sends an alarm condition notice to the dispatching system 14 where the dispatching system 14 receives the alarm condition notice at 102. In addition to sending an alarm condition notice to the dispatching system 14, the program passes from step 100 to step 104 where it is determined whether the pump 12 is configured to display a local alarm condition indicating that pump 12 is not connected to the dispatching system 14. If pump 12 is configured to display such a local alarm notice, the program passes to step 106 where such an alarm condition is displayed or otherwise indicated. If pump 12 is not configured to display such an alarm notice, the program passes to step 108 where action occurs, as will be discussed hereafter.

As mentioned above, when an alarm condition is generated at 26 and the pump 12 is connected to the dispatching system 14, an alarm condition message is sent at step 100 to the dispatching system 14 where it is received at step 102. At step 102, the alarm condition message is evaluated according to the rules, algorithms or instructions that determine whether the alarm condition message should be forwarded to the alarm forwarding system 16 or the monitor/controller system 18 or both. If, at step 102, it is determined that the alarm condition message should not be forwarded to either the alarm forwarding system 16 or monitor/controller system 18, the program passes to step 98 where the pump 12 will display or generate an alarm on the pump 12.

If, at step 102, it is determined that the alarm condition message should be forwarded to either the alarm forwarding system 16 or monitor/controller system 18, the program passes to step 110 in the alarm forwarding system 16. At step 110, the program determines, according to rules, algorithms or instructions, whether the alarm condition should be routed to a recipient and if so, which recipient. If it is determined that the alarm condition notice should be forwarded to a recipient, the program passes from step 110 in the alarm forwarding system 16 to step 112 in the monitor/controller system 18. In order for the program to reach step 110, an alarm condition message must have been received by the alarm forwarding system 16. Consequently, at step 110, the program passes to step 114 where it is determined whether the alarm forwarding system 16 is configured to send acknowledgment of a successful receipt of an alarm notice message. If the alarm forwarding system 16 is not configured to send such an acknowledgment, the program passes to 116 were no further action is taken. However, if the alarm forwarding system 16 is configured to send such an acknowledgement, the program passes to step 118 where such acknowledgment is generated by the alarm forwarding system 16 and sent to the dispatching system 14 to be received at step 120. If, at step 120, it is determined that the alarm condition message was successfully received by the alarm forwarding system 16, the program passes to step 108 in the pump 12.

If, at step 108, it is determined that the alarm condition message generated at step 100 was not received by the alarm forwarding system 16, the program passes to step 106 where an alarm condition indicating that the alarm condition message was not received by the alarm forwarding system 16 is displayed on the pump 12. If however, at step 108, it is determined that the alarm condition message generated step 100 was successfully received by the alarm forwarding system 16, the program passes to step 122 where no alarm is displayed locally on pump 12.

If, at step 120, it is determined that the alarm condition message received from pump 12 by the dispatching system 14 at step 102 has not been successfully forwarded to the alarm forwarding system 16, the program passes to an escalation scheme 40 where the appropriate level of escalation is determined according to rules, algorithms or instructions as discussed above. Also at step 120, if it is been determined that the alarm condition message generated by pump 12 and received by dispatching system 14 has also been successfully received by the alarm forwarding system 16, the program also passes to step 44 where the local delay timer 50 is canceled and no alarm message is generated.

If, in the monitor/controller system 18 at step 112, an alarm condition indication is indicated on a monitor/controlling system 18, the program passes to step 124 where the recipient of the alarm condition message is given the opportunity to acknowledge receipt of the alarm condition message. If the recipient chooses to generate an acknowledgment of the receipt of such a message, the program passes to step 126 in the alarm forwarding system 16 where the acknowledgement is passed to step 128 in the dispatching system 14. Step 128 ascertains whether the recipient has acknowledged receipt of the alarm condition message sent by pump 12. If the answer is yes, the program passes to step 130 where acknowledgment to send from the dispatching system 14 to step 44 where the local delay timer 50 is canceled and no alarm message is thus generated.

If an alarm condition indication is sent to a monitor/controlling system 18 at step 112, the program passes to step 132 where, according to rules, algorithms or instructions, it is ascertained whether the alarm condition is capable of remote clearing. If the alarm condition is not capable of remote clearing, the program passes to step 134 where no further action is taken. However, if the alarm condition is capable of remote clearing, the program passes to step 136 where the alarm may be cleared on the monitor/controlling system 18 by a qualified clinician.

The program then passes to step 138 in the alarm forwarding system 16. Step 138 passes the alarm clearing message to step 140 of the dispatching system 14 which passes the alarm clearing message to pump 12 at step 142. At step 142, the pump alarm is cleared on pump 12. If the pump alarm is cleared at step 142 on pump 12, the program passes to step 144 of the dispatching system 14. At step 144 the dispatching system 14 is notified that the alarm condition message previously generated by pump 12 at step 100 has been cleared remotely. The program then passes to step 146 on the alarm forwarding system 16 where a local alarm notification is sent to the appropriate recipients as determined by the rules, algorithms or instructions running on alarm forming system 16. Further, the program passes to step 148 in the monitor/controller system 18 where a local alarm condition is indicated on the appropriate monitor/controlling systems 18 indicating that an alarm condition notice has been cleared.

The program then passes to step 150 where it is determined whether the alarm condition has been resolved. If the alarm condition has been resolved, the program passes to step 152 on pump 12 where the alarm on pump 12 is cleared. If the program determined at step 150 that the alarm condition is not been resolved, the program passes to step 40 where an escalation scheme is entered into so that the appropriate action, according to the rules, algorithms or instructions previously determined, can be taken to resolve the alarm condition issue. At step 144, the program also passes to step 72 where, as described above, if the pump 12 is not configured to suppress a local edible alarm, pump 12 will provide a local audible alarm.

When an alarm gets cleared, either manually by a clinician or automatically according to the rules, algorithms or instructions running on the patient care system 10, a "clearing alarm message" may be sent to all the entities that received the original alarm. Such clearing alarm message may indicate how the alarm was cleared, when, and by whom and may include an indication of what the original alarm was, its timestamp and how the alarm was resolved. Further, although the alarm has been shown as being cleared in certain locations, the alarm may be cleared from wherever a clinician has access to the patient care system 10, whether at the pump 12, dispatching system 14, alarm forwarding system 16, clinical system server 24 or monitor/controlling system 18. It may be desirable to explicitly indicate or highlight on the pump 12 itself that the clearing took place remotely in order to alert the nearby attending personnel of the source of the clearing. In addition, if the alarm is locally cleared before it was cleared remotely, the dispatching system server 14 will receive notice of this occurrence and forward such notice to the remote recipients.

Further, it is desirable if the alarm is cleared remotely but not locally, that the local delay timer described above be employed to re-start the alarm sequence described herein after the expiration of a predetermined time in case a clinician clears the alarm remotely but forgets to check on the pump 12 and clear the alarm locally on the pump.

Figure 7:
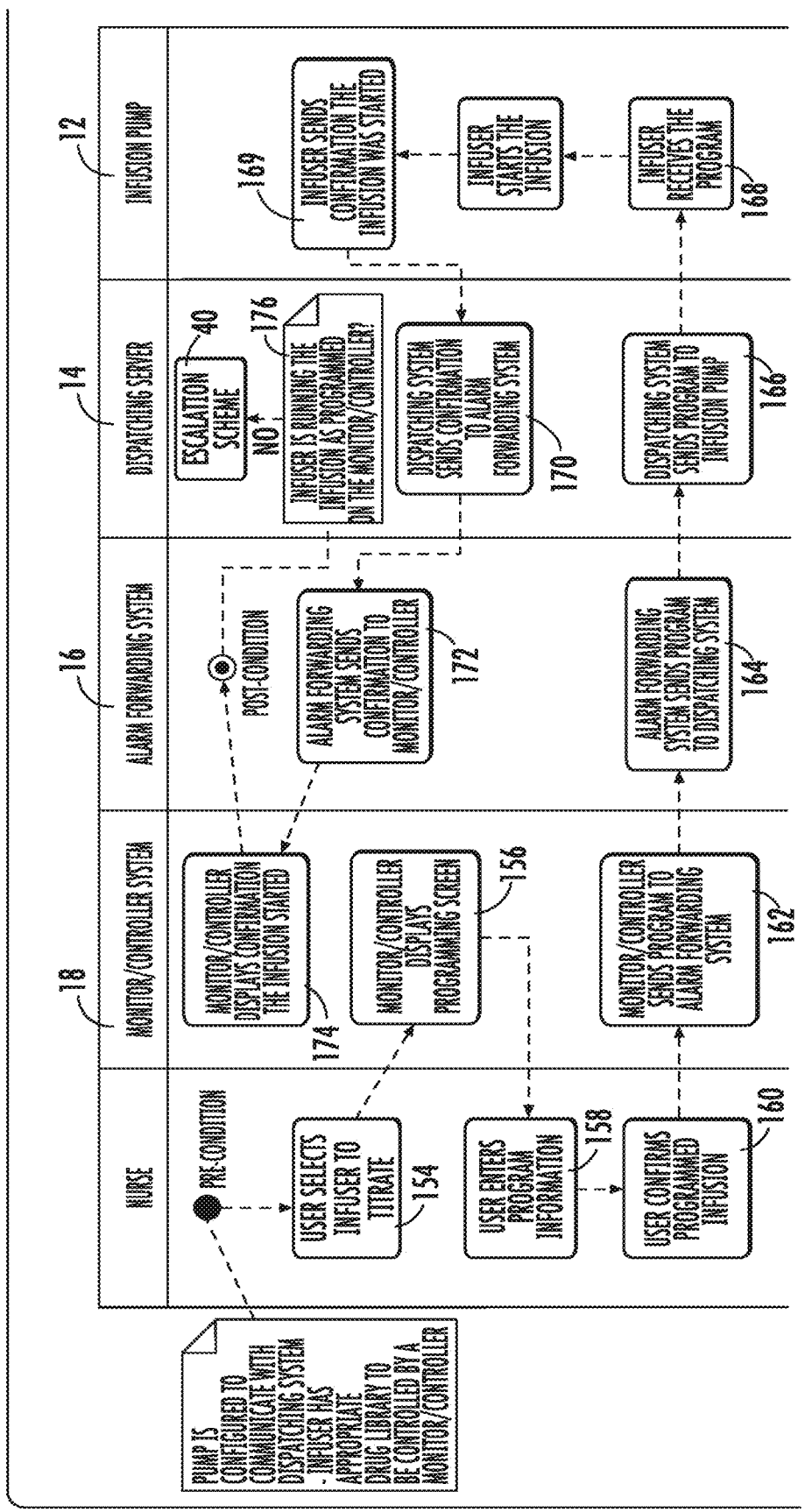

FIG. 7 illustrates an embodiment of the patient care system 10 where the infusion program operating on pump 12 is modified or replaced by an operator. In this embodiment of the patient care system 10, the pump 12 must be connected to the dispatching system 14 in order to be controlled by the monitor/controller system 18 as will be described hereafter. Further, the pump 12 must have an appropriate drug library with settings selected or configured by the manufacturer or more preferably the healthcare facility that allow the infusion program to be modified or replaced remotely from a monitor/controlling system for alarm management purposes. The drug library must be stored on the pump or otherwise be accessible to the pump 12. In this embodiment, an appropriate or authorized person, for example a nurse providing care to a patient, on their respective monitor/controller system 18 selects some aspect of the operation of the pump 12 with respect to the patient. For example, as shown in FIG. 7, at step 154, the clinician could select the infusion titrate. Consequently, at 156 the clinician accesses a programming screen on the monitor/controller 18. The clinician, at step 158, then enters the desired programming information on the programming screen of the monitor/controlling system 18. Thereafter, the process passes to step 160 where the clinician confirms the program information. The process then passes to step 162 where the monitor/controller system 18 sends the new program information to the alarm forwarding system 16 where it is received at step 164. At step 164, the alarm forwarding system sends the programming instructions to the dispatching system 14 where it is received at step 166. At step 166, the dispatching system 14 sends the program instructions to the infusion pump 12 where it is received and incorporated into the pump 12 at step 168. The pump 12 may act on the new or modified program instructions immediately as shown in FIG. 7 or may proceed in a delayed manner after local or remote confirmation.

As can be seen in the description of the patient care system 10, there are certain steps that are performed as part of the logic, whether software or by discrete logic on the various components of the patient care system 10 and pump 12. But, there are also certain steps that are performed by the clinician that are not part of or performed by such logic. Where a process involving the patient care system 10 involves steps performed by the clinician but that are not performed by the patient care system 10, whether in embodiments including the pump 12 or monitor/controller 18, the process steps performed by the clinician are not part of the patient care system 10.

Also as shown in FIG. 7, at 169 pump 12 sends confirmation to the dispatching system 14 that infusion by the pump 12 to the patient has started. The dispatching system 14 at 170 receives confirmation that the infusion by pump 12 was started and passes this information to the alarm forwarding system 16 at 172. At step 172, the alarm forwarding system 16 sends confirmation that the pump 12 has started infusion to the monitor/controller 18 at 174. At step 174, the monitor/controller system 18 displays a confirmation that the infusion by the pump 12 has started. At step 174, the monitor/controller system 18 displays that the infusion has started by the pump 12. This confirmation is also sent from the monitor/controller 18 to the dispatching system 14 at step 176 (via the alarm forwarding system 16). At step 176 the dispatching system 14 ascertains whether the infusion started by pump 12 is the desired infusion as programmed by the monitor/controller 18. If the infusion is not correct, the dispatching system 14 passes to step 40 where an escalation scheme is entered into and action taken according to the rules, algorithms or instructions set up in the escalation scheme.

Figure 8:
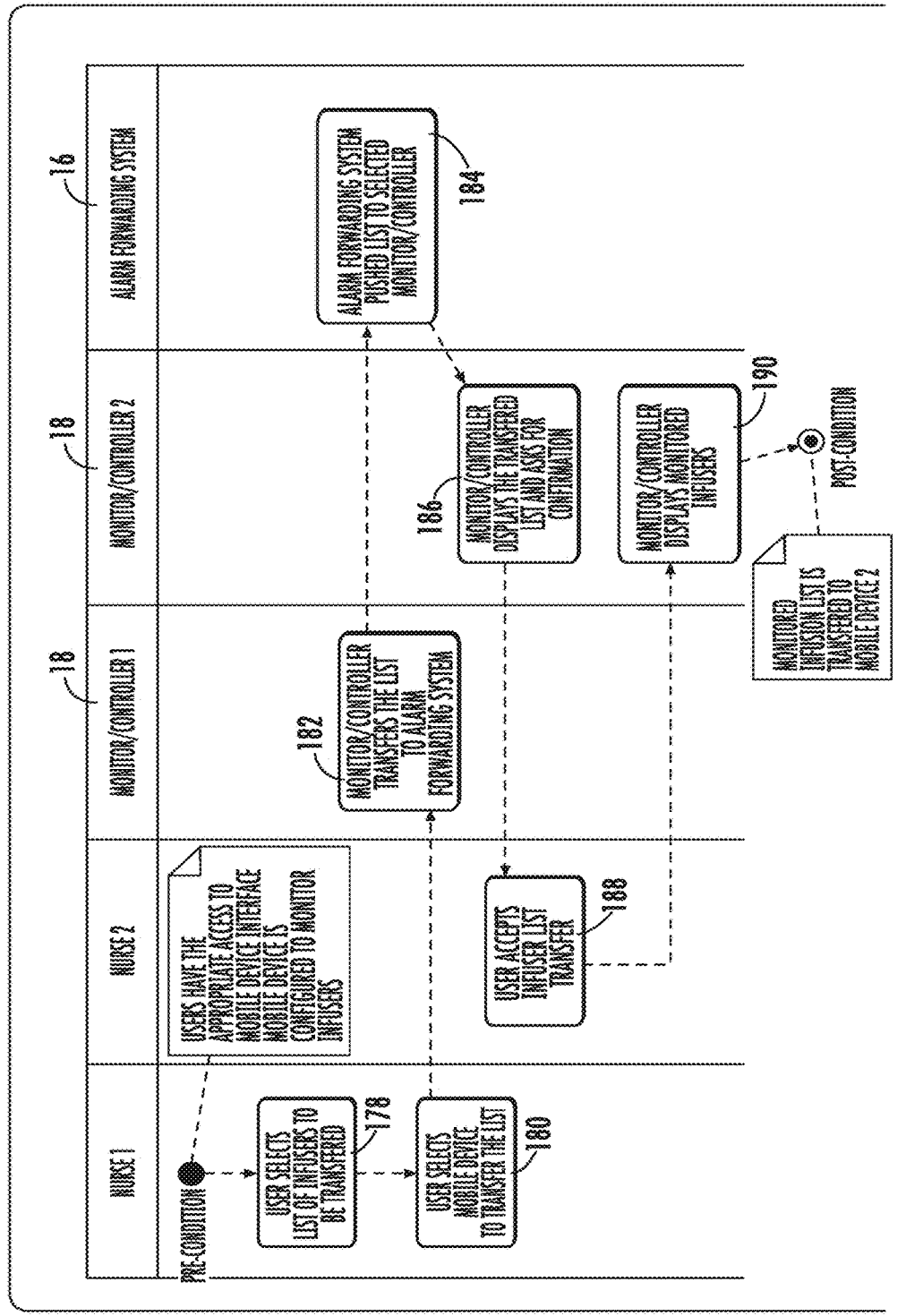
FIG. 8 is a chart of one embodiment of the patient care system showing the process of transferring oversight of one or more pumps from one monitor/controller system to another monitor/controlling system.

Another management function of the patient care system 10 is shown in FIG. 8. In this function, a clinician transfers responsibility for one or more pumps 12 to another clinician. To access this functionality, both the clinician doing the transferring and the clinician receiving the transfer of responsibility for the pumps 12 must have appropriate access to the dispatching system 14 and alarm forwarding system 16, for example, through each clinician's respective monitor/controlling systems 18 with their appropriate interfaces. By accessing the monitor/controller system 18, at 178 the clinician selects a list of pumps 12 to be transferred. The process passes to step 180 where the clinician selects the monitor/controlling system 18 to which the responsibility for the pumps 12 will be transferred.

The process passes to step 182 where the monitor/controller 18 for the person passing responsibility for the pumps 12 then transfers the list of selected pumps 12 to the monitor/controlling system 18 of the person receiving responsibility for the pumps 12 via the alarm forwarding system 16 where this information is received at 184. At step 184, the alarm forwarding system 16 pushes the list of selected pumps to the selected monitor/controller 18 receiving responsibility for the pumps 12 at 186. At 186, the respective monitor/controlling system 18 displays the transferred list of pumps 12 and ask for confirmation of the transfer. The clinician associated with the new responsibility for the pumps 12 then, on their monitor/controlling system 18, accepts the pump list transfer at 188. Also, as a result of the clinician accepting the pump 12 transfer list, the monitor/controller 18 of that clinician then displays the list of newly acquired pumps 12 at 190.

Figure 9:
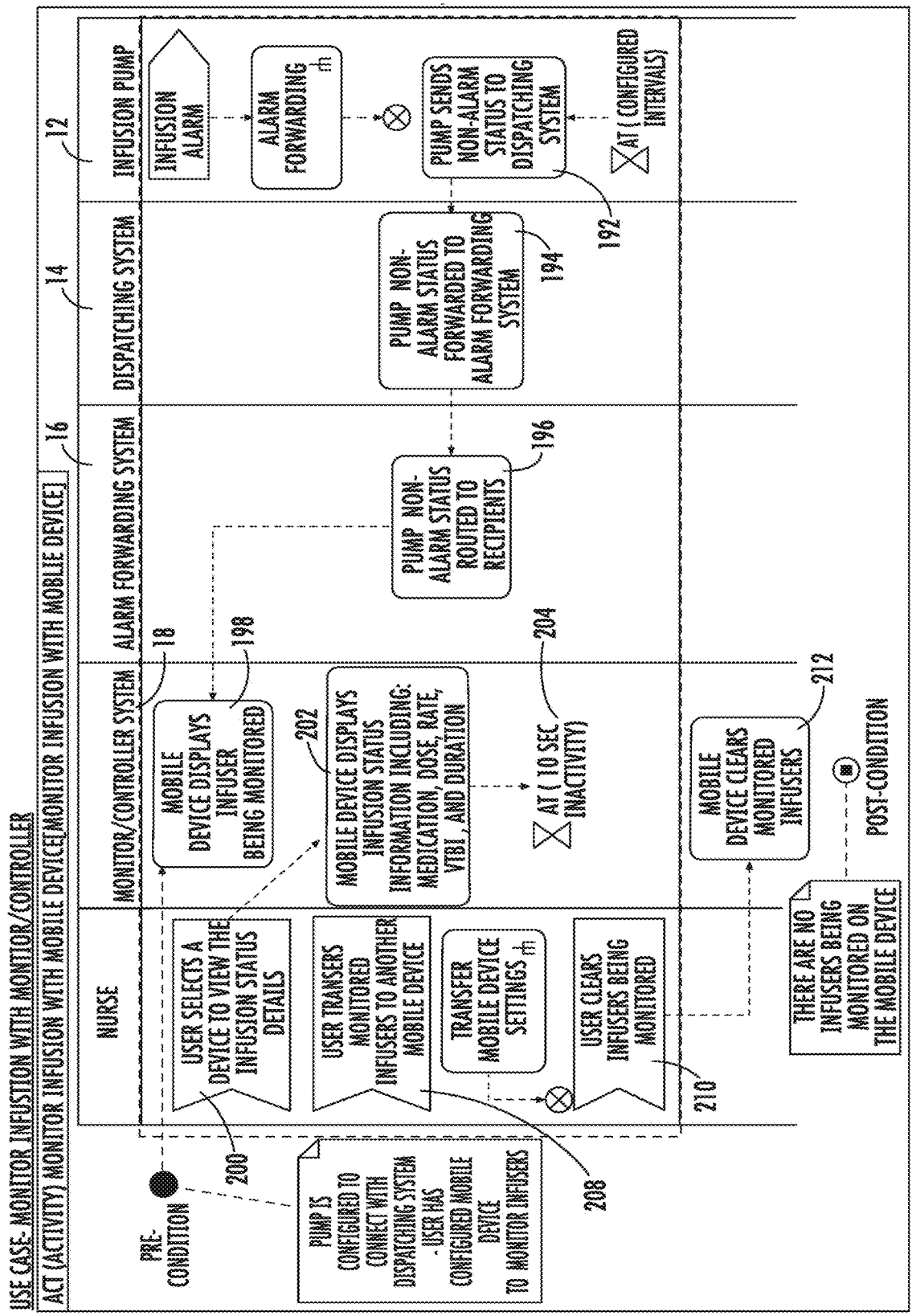
FIG. 9 is a chart of one embodiment of the patient care system showing the process of monitoring the infusion by a pump with a monitor/controlling system.

A monitor infusion function of the patient care system 10 is displayed in FIG. 9. Pump 12 is configured to interact with the dispatching system 14. At 192, pump 12 sends non-alarm status information to the dispatching system 14 where it is received at 194. Examples of such non-alarm status information include, but are not limited to, the medication being delivered, the dose, rate, volume to be infused (VTBI) and duration of infusion. Step 194 forwards the non-alarm status information from pump 12 to the alarm forwarding system 16 where it is received at 196. Step 196 then routes the pump 12 non-alarm status information to the appropriate recipient or recipients as configured by rules, algorithms or instructions operating on the alarm forwarding system 16. Each recipient of the pump 12 non-alarm status information receives this status information at step 198 on their respective monitor/controller system 18. As a result, the monitor/controller system 18 displays the non-alarm status information from pump 12 so that the clinician can be apprised of such status. If a particular clinician's monitor/controlling system 18 is monitoring more than one pump 12, it can be set to select and display individual information about each pump 12. At step 200, the clinician selects a pump 12 to view that pump 12's non-alarm status details. As a result of selecting a particular pump 12 to monitor, the monitor/controller system 18 at 202 displays the non-alarm infusion status information for that pump 12.

The patient care system 10 may also include functionality that affects the duration that certain information is displayed on the monitor/controller system 18. An example of such functionality is shown in FIG. 9. From 202, the program may pass to step 204 which is a timer that times the amount of inactivity associated with the clinician's interaction with the monitor/controller system 18. If a sufficiently long amount of time elapses according to rules, algorithms or instructions without the clinician interacting with the monitor/controller system 18 (e.g., 10 seconds), the program passes to step 206 where the monitor/controlling system 18 closes the detailed view of the non-alarm status information provided by a particular pump 12. Of course, the amount of time that must pass before activating this closing of the detailed view can vary and may be selectable by the clinician to suit the clinician's preference or may be preset according to certain safety protocols. Further, this functionality includes, in addition to the length of time certain information is displayed, also determining what information is displayed and for both, may take into consideration who the clinician is, what the pump status is and the location of the clinician.

As a result of having transferred responsibility for one or more pumps 12 to another monitor/controlling system 18, the clinician may clear their monitor/controlling system 18 of the transferred pumps 12. Of course, the clinician must first have transferred responsibility for the pumps 12 as is done at step 208 where the process described above is summarized into a single step 208. Thereafter, the program passes to 210 where the clinician clears the pumps 12 that have been transferred. The program then passes to step 212 where the monitor/controlling system 18 clears the previously monitored pumps 12 which have now been transferred to another clinician.

Figure 10:
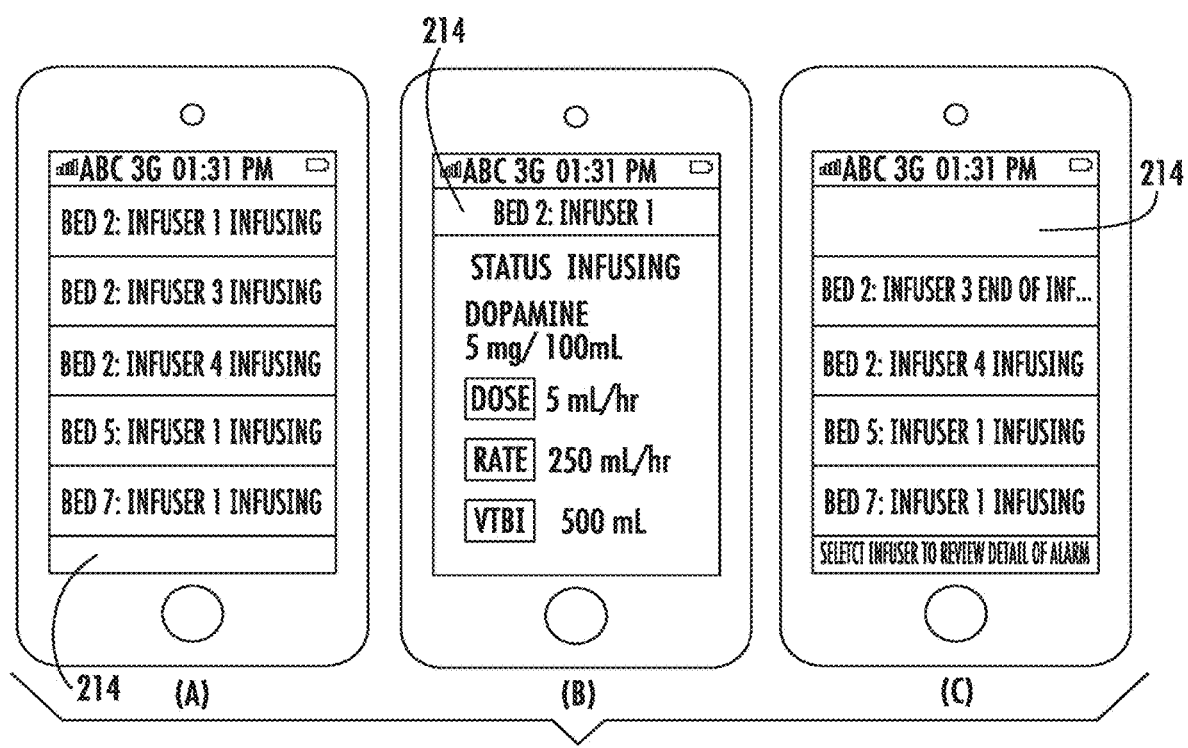
FIG. 10 is a top view of one embodiment of a monitor/controlling system user interface design in various states during operation.

FIG. 10 shows examples of the monitor/controlling system 18. Monitor/controlling system 18 may be a mobile phone, laptop computer, tablet or any other mobile device capable of interacting with the alarm forwarding system 16 and dispatching system 14, displaying information and allowing information to be entered and sent to the alarm forwarding system 16 and dispatching system 14. As can be seen in part A of FIG. 10, the status of devices being monitored located in several different locations (e.g., Bed 2, Bed 5 and Bed 7) can be displayed on a main status screen 214. The information displayed on the screen is the name of the pump 12 and the infusion status. Further as shown in part B of FIG. 10, the details of the infusion taking place by any particular pump 12 can be displayed once a pump 12 from the main status screen 214 is selected. For example, as can be seen in the example of part B of FIG. 10, where pump 12 is indicated as "Infuser 1" that is located at "Bed 2," the status "Infusing" is indicated as well as the drug being infused, in this case "Dopamine." Furthermore, the concentration of dopamine is indicated (5 mg/100 ml) as well as the dose (5 ml/hr), rate 10 (250 ml/hr) and VTBI (500 ml). A "patient" designation can of course be substituted for a "bed" designation without departing from the scope of the invention.

As shown in part C of FIG. 10, an alarm state can also be shown on the monitor/controller system 18. In this case, the pump 12 indicated as "Infuser 3" located at "Bed 2" is reaching the end of its infusion program. As a result, an "End of Infusion" 15 alarm message has been generated. One possible result of generating such an alarm message is that the monitor/controlling system 18 itself may indicate the alarm. In addition to indicating the status of particular pumps 12 (here, "End of Infusion"), the monitor/controlling system 18 may also activate a visual, audible or tactile alarm to alert the clinician of receipt of this alarm message.

Further, the order of display of the pumps 12 being monitored can be changed to represent the priority of their respective statuses. For example, as shown in part C of FIG. 10, the pump 12 designated "Infuser 3" at "Bed 2" is in a higher priority status than the other pumps 12 due to the presence of an alarm message associated with this particular pump 12. As a result, this pump 12 is listed higher on the display of the monitor/controlling system 18 than the other pumps 12 with lesser priority status in order to draw attention to this pump 12's heightened status.

Throughout this description, repeated mention has been made to "rules, algorithms or instructions." These rules, algorithms or instructions can be directed to virtually anything that is determined to be useful including, but not limited to, promoting safety or improving efficacy, longevity or ease of use. In addition, where the clinician is configuring or reconfiguring a pump 12, these rules, algorithms or instructions can include safeguards to warn clinicians if certain configurations are outside of accepted bounds or are dangerous so that the clinician may be required to confirm such configurations before they are accepted by the patient care system 10. Further, where, when and to whom alarm messages may be forwarded or communicated to may take into consideration the staff available, clinical care area (CCA), therapy being delivered, type of drug, condition of the patient, time of day, day of the week, whether there has been or is an alarm escalation scheme 40 in effect to name but a few possible considerations.

The patient care system 10 described herein, in one or more of the embodiments disclosed, has advantages over current systems in increased patient safety and increased case of use for the clinicians. With respect to increased patient safety, the patient care system 10 in one or more embodiments increases patient safety by sounding an alarm when the alarm forwarding does not reach clinical personnel or they are unable to respond to or acknowledge the alarm in a timely manner. In this way, the possibility of a clinician missing or failing to respond to an alarm is decreased. The possibility of a clinician missing or failing to respond to an alarm is also decreased, and thus patient safety is increased, by creating alarm escalation procedures that help medical personnel back up each other in case an initial alarm is missed or failed to be responded to. Further, patient safety increases with one or more embodiments of the patient care system 10 because reaction time by medical personnel to adverse infusion events or pending adverse infusion events is reduced. This reaction time is reduced by alerting medical personnel to such adverse event or pending adverse event even though the medical personnel is physically distant from the pump 12.

Additionally, patient safety is increased in one or more embodiments of the patient care system 10 by creating a system of alarm evaluation and dispatch that operates according to rules, algorithms or instructions so that alarm management logic is removed from the individual and various monitor/controller systems 18 and corresponding communication technology and is instead governed and controlled by a reduced set (in some cases, a single set) of rules, algorithms and instructions operating on a smaller number of devices (in some cases, on a single dispatching system 14).

Further, patient safety is increased in one or more embodiments of the patient care system 10 by allowing medical personnel to program or modify an infusion without exposing the patient to unnecessary contact or the requirement that the pump 12 be programmed at the pump 12 itself. Because the clinician does not need to be physically present or come in contact directly with the pump 12, the likelihood of contamination of the patient by the clinician is reduced. In addition, because the clinician does not need to be physically present or contact the pump 12 directly, the likelihood of cross contamination by multiple clinicians is reduced when multiple clinicians utilize the same infusion pump 12. In this way, the pump 12 is not contaminated by a clinician in the first place and even if the pump 12 were initially contaminated, cross-contamination is eliminated because subsequent clinicians do not need to come in contact with or be in close proximity to the pump 12 to change or modify programming on pump 12 or check the status of the pump 12 or an infusion program running on pump 12. If necessary confirmations or double checks of program values previously done at the pump 12 can be done by the clinician on the monitor/controlling system 18.

In yet other embodiments of the patient care system 10, patient safety increases by reducing the chance of incorrect therapy delivery. The chance of delivering an incorrect therapy is reduced because the clinician need only become familiar with a single interface (monitor/controlling system 18) instead of needing to gain familiarity with the interfaces on a large number of devices which might be involved in therapy delivery. Further, the chance of delivering an incorrect therapy is reduced in one or more embodiments because there are checks built into the rules, algorithms or instructions implemented on the patient care system 10.

The patient care system 10 also increases case of use for the clinicians. With respect to increasing case of use, in one or more embodiments of the patient care system 10, patient care system 10 allows medical personnel to clear alarms remotely instead of requiring the personnel to move to the pump 12 to clear the alarm. Further, in one or more embodiments of the patient case system 10, case of use for medical personnel is increased by reducing the time necessary and the difficulty involved in modifying or updating programming and infusion program updates. Besides producing a simplified process for modifying or updating such programming, case of use is increased by requiring the clinician to become familiar with only a single interface (e.g., monitor/controlling system 18) instead of the interfaces for each device that might be involved in therapy delivery.

In addition, the patient care system 10, in one or more embodiments, increases case of use for medical personnel by sending alarm messages to medical personnel even 5 when they are not in proximity of the device (i.e., they are outside of visual and acoustic range of the pump 12). Further, in one or more embodiments, information that is useful or needed by the medical personnel about an alarm message such as the pump 12 ID, pump 12 location, patient information, drug information, program information, etc. are provided with the alarm message to aid such personnel in evaluating the alarm. As a result, medical personnel can have greater range from their patients and still deliver safe and effective therapy.

Another aspect of the patient care system 10 that increases case of use for medical personnel in one or more embodiments of the patient care system 10 is that alarm noise in the hospital is reduced, which is beneficial-especially at night time. The reduction in alarm noise is due to the processing of alarms according to rules, algorithms or instructions to eliminate false or unnecessary alarms thereby producing fewer audible or visual alarms. Reducing the number of annoying distracting, false or unnecessary alarms benefits not only the medical personnel but the patient and other nearby patients as well.

Not all of these advantages will be present in every embodiment of the patient care system 10; some embodiments may have only one of these advantages while other embodiments will have more than one advantage and some embodiments may have all of the advantages. The disclosure has been directed to certain embodiments, combinations, configurations and relative dimensions. It is to be understood, however, that the description given herein has been given for the purpose of explaining and illustrating the invention and are not intended to limit the scope of the invention. It is to be further understood that changes and modifications to the descriptions given herein will occur to those skilled in the art. Therefore, the scope of the invention should be limited only by the scope of the claims.

What is claimed is:

1. A system for reducing audible alarms generated at an infusion pump, the system comprising one or more hardware processors configured to:
   delay any alarms corresponding to an alarm condition at the infusion pump for a predetermined time period responsive to the alarm condition being forwarded to a remote computing system;
   determine that the alarm condition was not addressed at the remote computing system after the predetermined time period has elapsed; and display, at the infusion pump, a visual indication of the alarm condition based on the determination that the alarm condition is present after the predetermined time period has elapsed; and generate, at the infusion pump, an audible alarm based on the determination that the alarm condition is present after the predetermined time period has elapsed.

2. The system of claim 1, wherein the remote computing system is configured to:
receive the alarm condition transmitted by a first computing system associated with the infusion pump; and
dispatch the alarm condition to one or more care provider computing systems,
said remote computing system is remote from a network of the first computing system.

3. The system of claim 1, wherein the remote computing system is further configured to transmit the alarm condition to a clinician computing device designated for the infusion pump.

4. The system of claim 3, wherein the remote computing system is further configured to change the clinician computing device designated for the infusion pump to a secondary clinician device based on a lack of response from the clinician computing device, thereby enabling the secondary clinician device to monitor the infusion pump.

5. The system of claim 3, wherein the clinician computing device is changed in response to a request for change.

6. The system of claim 3, wherein the clinician computing device is changed in response to escalation of the alarm condition.

7. The system of claim 1, wherein the time period is based on a clinical care area in which the infusion pump is located.

8. The system of claim 7, wherein the clinical care area is determined based on an identification data associated with the infusion pump.

9. The system of claim 3, wherein the clinician computing device is changed in response to a determination that a transmission to the clinician computing device failed.

10. A method for reducing audible alarms generated at an infusion pump, the method comprising:
delaying an audible alarm corresponding to an alarm condition at the infusion pump for a predetermined time period responsive to the alarm condition being forwarded to a remote computing system;
determining that the alarm condition was not addressed at the remote computing system after the time period has elapsed; and
generating, at the infusion pump, an audible alarm based on the determination that the alarm condition is present after the predetermined time period has elapsed.

11. The method of claim 10, further comprising:
receiving, at the remote computing system, the alarm condition transmitted by a first computing system associated with the infusion pump; and
dispatching, by the remote computing system, the alarm condition to one or more care provider computing systems,
said remote computing system is remote from a network of the first computing system.

12. The method of claim 11, further comprising transmitting the alarm condition from the remote computing system to a clinician computing device designated for the infusion pump.

13. The method of claim 12, further comprising changing the clinician computing device designated for the infusion pump to a secondary clinician device based on a lack of response from the clinician computing device, thereby enabling the secondary clinician device to monitor the infusion pump.

14. The method of claim 12, wherein the clinician computing device is changed in response to a request for change.

15. The method of claim 12, wherein the clinician computing device is changed in response to escalation of the alarm condition.

16. The method of claim 11, wherein the time period is based on a clinical care area in which the infusion pump is located.

17. The method of claim 16, wherein the clinical care area is determined based on an identification data associated with the infusion pump.

18. The method of claim 12, wherein the clinician computing device is changed in response to a determination that a transmission to the clinician computing device failed.

* * * * *